(12) United States Patent
Chen et al.

(10) Patent No.: US 10,815,232 B2
(45) Date of Patent: Oct. 27, 2020

(54) CRYSTALLINE FORMS OF VIRAL-PROTEIN INHIBITOR DRUG VX-787, PROCESSES FOR PREPARATION THEREOF AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Lie Chen, Suzhou (CN); Chaohui Yang, Suzhou (CN); Nan Xia, Suzhou (CN); Xiaoyu Zhang, Suzhou (CN); Chunxiang Huang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/480,470

(22) PCT Filed: Jan. 24, 2018

(86) PCT No.: PCT/CN2018/074050
§ 371 (c)(1),
(2) Date: Jul. 24, 2019

(87) PCT Pub. No.: WO2018/137670
PCT Pub. Date: Aug. 2, 2018

(65) Prior Publication Data
US 2019/0352303 A1   Nov. 21, 2019

(30) Foreign Application Priority Data

Jan. 24, 2017 (CN) .......................... 2017 1 0060189
Jan. 24, 2017 (CN) .......................... 2017 1 0060196

(51) Int. Cl.
*C07D 471/04* (2006.01)
*A61P 31/16* (2006.01)

(52) U.S. Cl.
CPC ............ *C07D 471/04* (2013.01); *A61P 31/16* (2018.01); *C07B 2200/13* (2013.01)

(58) Field of Classification Search
CPC .... C07D 471/04; C07B 2200/13; A61P 31/16
See application file for complete search history.

(56) References Cited

FOREIGN PATENT DOCUMENTS

| CN | 105848683 | 8/2016 |
| CN | 105849100 | 8/2016 |
| WO | 2015/120097 | 8/2015 |
| WO | 2018191475 A1 * | 10/2018 |

OTHER PUBLICATIONS

Solid State Characterization of Pharmaceuticals, p. 63 (R.A. Storey et al., eds., 2011) (Year: 2011).*
S. Bhattacharya, et al., Thermoanalytical and Crystallographic Methods, in Polymorphism in Pharmaceutical Solids, 318-346 (H.G. Brittain ed., 2nd ed., 2009) (Year: 2009).*
H.G. Brittain, Preformulation in Solid Dosage Form Development (M. C. Adeyeye et al., eds., 2008) (Year: 2008).*
Bighley-Swarbrick, Ency. Pharm. Technology Ch. 13, (Marcel Dekker, NY1996) (Year: 1996).*
ISA/CN, International Search Report for PCT/CN2018/074050 (dated Apr. 18, 2018)—English translation.

* cited by examiner

*Primary Examiner* — Mark L Shibuya
*Assistant Examiner* — Ebenezer O Sackey
(74) *Attorney, Agent, or Firm* — Fish & Richardson P.C.

(57) ABSTRACT

The present disclosure relates to novel crystalline forms of VX-787, processes for preparation thereof and use thereof. VX-787 is a viral-protein inhibitor drug. The present disclosure provides crystalline form CS1, crystalline form CS2, crystalline form CS3, and crystalline form CS4 of compound (I) hydrochloride. The present disclosure also provides crystalline form CS3 and crystalline form CS9 of compound (I).free form.

19 Claims, 14 Drawing Sheets

Compound I

CRYSTALLINE FORMS OF VIRAL-PROTEIN INHIBITOR DRUG VX-787, PROCESSES FOR PREPARATION THEREOF AND USE THEREOF

CROSS-REFERENCE TO RELATED APPLICATIONS

This application is a U.S. national stage application under 35 U.S.C. § 371 of International Application No. PCT/CN2018/074050 filed on Jan. 24, 2018, which claims the benefit of foreign priority to Chinese patent application No. 201710060189.7 filed on Jan. 24, 2017 and Chinese patent application No. 201710060196.7 filed on Jan. 24, 2017, the contents of which are incorporated herein by reference in their entirety.

TECHNICAL FIELD

The present disclosure relates to the field of pharmaceutical crystal, particularly relates to crystalline forms of viral-protein inhibitor drug VX-787, processes for preparation thereof and use thereof.

BACKGROUND

Influenza. A virus is a common influenza virus. It is highly pathogenic to human and has caused many worldwide pandemics. The subtype of influenza A virus is called "avian influenza". Avian influenza is an acute infectious disease caused by avian influenza virus. Avian influenza virus can infect human after gene mutation. The main symptoms after infection are high fever, cough, runny nose and myalgia, etc. Avian influenza usually result in severe pneumonia. Severe avian influenza can cause multiple organ failure, such as heart failure and renal failure, and result in death. The mortality rate is high.

VX-787 or JNJ-872 is a viral-protein inhibitor, it was developed by Vertex, and later authorized to Janssen Pharmaceutical Co. Ltd for co-development. The compound is currently in the clinical stage for the treatment of influenza A. Preliminary clinical evaluation shows that VX-787 is very promising. Phase I studies showed that VX-787 had good tolerance. Completed Phase IIa studies have shown that VX-787 showed a statistical significance in virological and clinical evaluation of influenza virus infection. The chemical name of VX-787 is (2S,3S)-3-((5-Huoro-2-(5-fluoro-1.171-pyrrolo[2,3-b]pyridin-3-yl)pyrimidin-4-yl)amino) bicyclo[2.2.2]octane-2-carboxylic acid, and the structure is shown as follows:

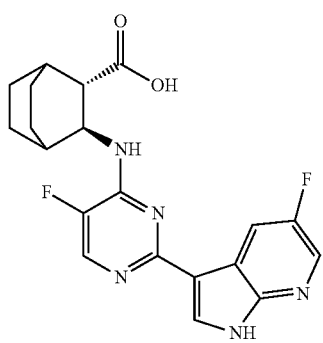

Compound I

Different crystalline forms of solid chemical drugs can lead to differences in their solubility, stability, flowability and compressibility, thereby affecting the safety and efficacy of pharmaceutical products containing the compounds (see K. Knapman, Modern Drug Discovery, 3, 53-54, 57,2000), which results in differences in clinical efficacy. The discovery of new crystalline forms (including anhydrates, hydrates, solvates, etc.) of the active pharmaceutical ingredients may provide drug substance with processing advantages and better physical and chemical properties such as better bioavailability, better storage stability, easiness to process, and easiness to purify. Some novel crystalline forms may serve as intermediate crystal forms to facilitate solid state transformation to desired forms. Novel polymorphs of raw materials can enhance the performance of the drug and provide more solid states in the formulation, and this can improve dissolution, improve shelf life, and make it easier to process.

CN105849100A disclosed hemihydrate crystalline form A, trihydrate crystalline form F and crystalline form D of compound I hydrochloride. The preparation process of crystalline form A needs a 0.05-0.85 water activity. Crystalline form D is a dehydration products of crystalline form A. The preparation process of crystalline form F needs a water activity equal to or greater than 0.9. The storage condition of crystalline form F is strict. It was disclosed in CN105849100A that crystalline form A is the preferred crystalline form. Meanwhile, CN105849100A disclosed crystalline form A and crystalline form B of compound 1 free form. It is disclosed in the text that the hydrate crystalline form B of compound I free form and the crystalline form A of compound I free base are the same crystalline form, but the preparation method of crystalline form B is more complicated.

Therefore, it is still necessary to systematically and comprehensively develop different crystalline and salt forms of compound I in order to realize its pharmacological development, release its potential, and promote the preparation of better formulations of the active drug ingredients. The crystalline form CS1, crystalline form CS2, crystalline form CS3, and crystalline form CS4 of compound I hydrochloride and crystalline form CS3 and crystalline form CS9 of compound I provided by the disclosure are simple in preparation method, and have advantages in stability, mechanical stability, hygroscopicity, solubility, purification and so on. The present disclosure provides a new and better choice for the preparation of pharmaceutical preparations containing compound I and is of great significance for drug development.

SUMMARY

In order to solve the above problems, the present disclosure provides crystalline forms of compound I hydrochloride, processes for preparation thereof and use thereof.

According to one objective of the present disclosure, crystalline forms of compound I hydrochloride are provided.

The X-ray powder diffraction pattern of crystalline form of compound I hydrochloride show characteristic peaks at 2 theta values of 7.1°±0.2°, 27.0°±0.2° and 15.7±0.2° using CuKα radiation.

Furthermore, the X-ray powder diffraction pattern of crystalline form of compound I hydrochloride shows one or two or three characteristic peaks at 2 theta values of 25.8°±0.2°, 14.7°±0.2° and 23.9°±0.2° using CuKα radiation. Preferably, the X-ray powder diffraction pattern of hydrochloride crystalline forts shows three characteristic peaks at 2 theta values of 25.8°±0.2°, 14.7°±0.2° and 23.9°±0.2° using CuKα radiation.

Furthermore, the X-ray powder diffraction pattern of crystalline form of compound I hydrochloride shows one or two or three characteristic peaks at 2 theta values of 17.5°±0.2°, 13.5°±0.2° and 28.7°±0.2° using CuKα radiation. Preferably, the X-ray powder diffraction pattern of hydrochloride crystalline form shows three characteristic peaks at 2 theta values of 17.5°±0.2°, 13.5°±0.2° and 28.7±0.2° using CuKα radiation.

In a preferred embodiment, the X-ray powder diffraction pattern of crystalline form of compound I hydrochloride shows characteristic peaks at 2 theta values of 7.1°±0.2°, 27.0°±0.2°, 15.7±0.2°, 25.8°±0.2°14.7°, 10.2°, 23.9°±0.2°, 17.5°±0.2°, 13.5°±0.2°, 28.7°±0.2°, 6.7°±0.2°, 7.6°±0.2°, 9.8°±0.2°, 10.7±0.2°, 18.6°±0.2° and 21.6°±0.2° using CuKα radiation.

Furthermore, said crystalline form of compound I hydrochloride have isomorphism. On the one hand, said crystalline form of compound I hydrochloride is compound hydrochloride Form CS3.

Without any limitation being implied, the X-ray powder diffraction pattern of hydrochloride Form CS3 is substantially as depicted in FIG. 1.

Without any limitation being implied, in a specific embodiment, the Differential Scanning calorimetry (DSC) curve of hydrochloride Form CS3 is substantially as depicted in FIG. 2, which shows two endothermic peaks. The first endothermic peak is at around 54° C. (onset temperature), and the second endothermic peak is at 200° C. (onset temperature).

Without any limitation being implied, in a specific embodiment, the Thermal Gravimetric Analysis (TGA) curve of hydrochloride Form CS3 is substantially as depicted in FIG. 3, which shows about 4.8% weight loss when heated to 120° C., and shows about 7.5% weight loss when further heated to 230° C.

Without any limitation being implied, hydrochloride Form CS3 is a hydrate.

According to the objective of the present disclosure, a process for preparing Form CS3 of compound I hydrochloride is also provided. The process comprises: placing crystalline form CS1 of compound I hydrochloride into inert atmosphere, heating to 100-200° C. and keeping for 5-20 minutes, and transferring the sample to room temperature to obtain hydrochloride Form CS3.

Furthermore, said heating rate is 1-20° C./min, preferably 10° C./min, the inert atmosphere is preferably nitrogen atmosphere, and the heating temperature is preferably 150° C.

Hydrochloride Form CS3 of the present disclosure has the following advantages:
1. High solubility. In the saturated aqueous solution, hydrochloride Form CS3 of the present disclosure has 6-51 times higher solubility than Form A of CN105849100 A at 1 h, 4 h and 24 h time point. Higher solubility of hydrochloride Form CS3 is beneficial to ensure the efficacy of the drug, reduce the dosage of the drug, thereby reducing the side effects of the drug and improving the safety of the drug. At the same time, higher solubility of hydrochloride Form CS3 helps to improve the dissolution rate and reduce the difficulty in the development of the formulation process.
2. Good stability, Hydrochloride Form CS3 of the present disclosure is stable for at least two weeks under the conditions of 2.5° C./60% RH. 40° C./75% RH and 60° C./75% M, preferably at least 1 month, and more preferably at least 7 months. Crystalline form and chemical purity remain substantially unchanged during storage. A better stability of hydrochloride Form CS3 can reduce the risk of drug dissolution rate and bioavailability change due to the change of crystalline forms, which is of great significance to ensure the efficacy and safety of drugs and prevent adverse drug reactions. Hydrochloride Form CS3 with better stability is controllable during the crystallization, formulation and storage process and not easy to produce mixed crystal, which is of great value for industrial production.

On the other hand, said crystalline form of compound I hydrochloride is hydrochloride Form C Si.

Without any limitation being implied, the X-ray powder diffraction pattern of hydrochloride Form CS1 is substantially as depicted in FIG. 4.

Without any limitation being implied, in a specific embodiment, the DSC curve of hydrochloride Form CS1 is substantially as depicted in FIG. 5, which shows two endothermic peaks. The first endothermic peak is at around 40° C. (onset temperature), and the second endothermic peak is at around 202° C. (onset temperature).

Without any limitation being implied, in a specific embodiment, the TGA curve of hydrochloride Form CS1 is substantially as depicted in FIG. 6, which shows about 11.2% weight loss when heated to 160° C., and about 6.7% weight loss when further heated to 220° C.

Without any limitation being implied, said hydrochloride Form CS1 is an acetic acid solvate.

According to the objective of the present disclosure, a process for preparing Form CS1 of compound I hydrochloride is also provided. The process comprises:
1) Adding compound I to acetic acid, stirring at 5-30° C. for 10-100 minutes, adding a certain amount of hydrochloric acid, stirring for 6-48 hours, filtering and drying to obtain a solid, or
2) Adding compound I hydrochloride to acetic acid, stirring at 5-30° C. for 6-48 hours, filtering and drying to obtain hydrochloride Form CS1.

Furthermore, in method 1), the molar ratio of compound I added to hydrochloric acid added is 5/1-1/5; and the stirring temperature is preferably 25° C.

Furthermore, said stirring temperature in method 2) is preferably 25° C.

Hydrochloride Form CS1 of the present disclosure has the following advantages:
1. Good stability. Hydrochloride Form CS1 of the present disclosure is stable for at least 1 month under the conditions of 25° C./60% RH and 40° C./75% RH. Crystalline form and chemical purity remain substantially unchanged during storage. A better stability of hydrochloride Form CS1 can reduce the risk of drug dissolution rate and bioavailability change due to the change of crystalline forms, which is of great significance to ensure the efficacy and safety of drugs and prevent adverse drug reactions. Hydrochloride Form CS1 with better stability is controllable during the crystallization, formulation and storage process and cannot convert to mixed crystals easily, which is of great value for industrial production.
2. Good mechanical stability. No crystalline form change of hydrochloride Form CS1 was observed after grinding. Good mechanical stability of hydrochloride Form CS1 makes it less demanding on crystallization equipment, requires no special post-treatment conditions, and is more stable during the formulation process, which can reduce the development cost of the drug products and improve the quality of the drug.

According to another objective of the present disclosure, Form CS2 of compound I hydrochloride are provided.

The X-ray powder diffraction pattern of hydrochloride Form CS2 shows characteristic peaks at 2 theta values of 25.0°±0.2°, 22.2°±0.2° and 17.0°±0.2° using CuKα radiation. Furthermore, the X-ray powder diffraction pattern of hydrochloride Form CS2 shows one or two or three characteristic peaks at 2 theta values of 25.9°±0.2°, 16.1°±0.2° and 8.0°±0.2° using CuKα radiation. Preferably, the X-ray powder diffraction pattern of hydrochloride Form CS2 shows three characteristic peaks at 2 theta values of 25.9°±0.2°, 16.1°±0.2° and 8.0°±0.2° using CuKα radiation. Furthermore, the X-ray powder diffraction pattern of hydrochloride Form CS2 shows one or two or three characteristic peaks at 2 theta values of 29.2°±0.2°, 15.1°±0.2° and 21.1°±0.2° using CuKα radiation. Preferably, the X-ray powder diffraction pattern of hydrochloride Form CS2 shows three characteristic peaks at 2 theta values of 29.2°±0.2°, 15.1°±0.2° and 21.1°±0.2° using CuKα radiation. In a preferred embodiment, the X-ray powder diffraction pattern of hydrochloride Form CS2 shows characteristic peaks at 2 theta values of 25.0°±0.2°, 22.2°±0.2°, 17.0°±0.2°, 25.9°±0.2°, 16.1°±0.2°, 8.0°±10.2°, 29.2°±0.2°, 15.1°±0.2° and 21.1°±0.2° using CuKα radiation.

Without any limitation being implied, the X-ray powder diffraction pattern of hydrochloride Form CS2 is substantially as depicted in FIG. 7.

Without any limitation being implied, in a specific embodiment, the DSC curve of hydrochloride Form CS2 is substantially as depicted in FIG. 8, which shows two endothermic peaks. The first endothermic peak is at around 51° C. (onset temperature), and the second endothermic peak is at 196° C. (onset temperature).

Without any limitation being implied, in a specific embodiment, the TGA curve of hydrochloride Form CS2 is substantially as depicted in FIG. 9, which shows about 9.4% weight loss when heated to 140° C., and shows about 16.7% weight loss when further heated to 230° C.

According to the objective of the present disclosure, a process for preparing hydrochloride Form CS2 is also provided. The process comprises: adding compound I to chloroform at 5-30° C., stirring for 10-100 minutes, adding a certain amount of hydrochloric acid, stirring for 6-48 hours, filtering and drying the solid to obtain hydrochloride Form CS2.

Furthermore, said stirring temperature is preferably 25 the molar ratio of compound I added to hydrochloric acid added is 5/1-1/5, preferably 1/1.

According to another objective of the present disclosure, Form CS4 of compound hydrochloride are provided, hereinafter refers to hydrochloride Form CS4.

The X-ray powder diffraction pattern of hydrochloride Form CS4 shows characteristic peaks at 2 theta values of 8.0°±0.2°. 4.7°±0.2°. 20.6°±0.2° and 11.6°±0.2° using CuKα radiation.

Furthermore, the X-ray powder diffraction pattern of hydrochloride Form CS4 shows one or two or three characteristic peaks at 2 theta values of 16.4°±0.2°, 17.1°±0.2° and 12.7°±0.2° using CuKα radiation. Preferably, the X-ray powder diffraction pattern of hydrochloride Form CS4 shows three characteristic peaks at 2 theta values of 16.4°±0.2°, 17.1°±0.2° and 12.7°±0.2° using CuKα radiation.

In a preferred embodiment, the X-ray powder diffraction pattern of hydrochloride Form CS4 shows characteristic peaks at 2 theta values of 8.0°±0.2°, 4.7°±0.2°, 20.6°±0.2°, 11.6°±0.2°, 16.4°±0.2°, 17.1°±0.2° and 12.7°+0.2° using CuKα radiation. Without any limitation being implied, in a specific embodiment, the X-ray powder diffraction pattern of hydrochloride Form CS4 is substantially as depicted in FIG. 10.

Without any limitation being implied, in a specific embodiment, the DSC curve of hydrochloride Form CS4 is substantially as depicted in FIG. 11, which shows one endothermic peak and one exothermic peak. The endothermic peak is at around 48° C. (onset temperature), and the exothermic peak is at 186° C. (onset temperature).

Without any limitation being implied, in a specific embodiment, the TGA curve of hydrochloride Form CS4 is substantially as depicted in FIG. 12, which shows about 9.6% weight loss when heated to 120° C., and shows about 4.8% weight loss when further heated to 230° C.

According to the objective of the present disclosure, a process for preparing hydrochloride Form CS4 is also provided. The process comprises: adding compound I hydrochloride to a solvent mixture comprising alcohols and water, and stirring at 5-30° C. for 1-7 days, filtering and drying to obtain hydrochloride Form CS4.

Furthermore, said volume ratio of the alcohol to water is 19/1-1/19, preferably 3/1; and said stirring temperature is preferably 25° C.

Furthermore, said alcohol is preferably isopropyl alcohol.

Hydrochloride Form CS4 of the present disclosure has the following advantages:

1. Good stability, Hydrochloride Form CS4 of the present disclosure is stable for at least two weeks under the conditions of 25° C./60% RH, 40° C./75% RH and 60° C./75% RH, preferably at least 1 month, and more preferably at least 6 months. Crystalline form and chemical purity remain substantially unchanged during storage. A better stability of hydrochloride Form CS4 can reduce the risk of drug dissolution rate and bioavailability change due to the change of crystalline forms, which is of great significance to ensure the efficacy and safety of drugs and prevent adverse drug reactions. Hydrochloride Form CS4 with better stability is controllable during the crystallization, formulation and storage process and not easy to produce mixed crystal, which is of great value for industrial production.
2. Good purification effect. The purity of hydrochloride form A of CN105849100A is 97.91%, and the purity of the hydrochloride Form CS4 of the present invention is 99.70%, which is higher. The purity of the drug substance is important for ensuring the efficacy and safety of the drug product and preventing the adverse drug reactions. At the same time, the higher purity the drug substance has, the more stable the yield is and the easier the industrial production is,
3. High solubility. In the saturated aqueous solution, hydrochloride Form CS4 of the present disclosure has 38-283 times higher solubility than hydrochloride Form A of CN105849100A. Higher solubility of hydrochloride Form CS4 can reduce the dosage of the drug, thereby reducing the side effects of the drug and improving the safety of the drug. At the same time, higher solubility of hydrochloride Form CS4 helps to improve the dissolution rate and reduce the difficulty in the development of the formulation process.

According to the objective of the present disclosure, a pharmaceutical composition is provided, said pharmaceutical composition comprises a therapeutically effective amount of hydrochloride Form CS1, hydrochloride Form CS3 hydrochloride Form CS4 or combinations thereof and pharmaceutically acceptable carriers, diluents or excipients.

Furthermore, hydrochloride Form CST, hydrochloride Form CS3, hydrochloride Form CS4 or combinations thereof can be used for preparing drugs inhibiting virus protein.

Furthermore, hydrochloride Form CS1, hydrochloride Form CS3, hydrochloride Form CS4 or combinations thereof can be used for preparing drugs treating influenza A.

According to another objective of the present disclosure, crystalline form CS9 of compound I is provided.

The X-ray powder diffraction pattern of crystalline form CS9 shows characteristic peaks at 2 theta values of 16.4°±0.2°, 7.7°±0.2° and 8.6°±0.2° using CuKα radiation. Furthermore, the X-ray powder diffraction pattern of crystalline form CS9 shows one or more characteristic peaks at 2 theta values of 5.4°±0.2°, 18.4°±0.2°, 19.7°±0.2° and 12.6°±0.2° using CuKα radiation, Preferably, the X-ray powder diffraction pattern of crystalline form CS9 shows characteristic peaks at 2 theta values of 5.4°±0.2°, 18.4°±0.2°, 19.7°+0.2° and 12.6°±0.2° using CuKα radiation.

In a preferred embodiment, the X-ray powder diffraction pattern of crystalline form CS9 shows characteristic peaks at 2 theta values of 16.4°±0.2°, 7.7°±0.2°, 8.6°±0.2°, 5.4°±0.2°, 18.4°±0.2°, 19.7°±0.2° and 12.6°±0.2° using CuKα radiation.

Without any limitation being implied, in a specific embodiment, the X-ray powder diffraction pattern of crystalline form CS9 is substantially as depicted in FIG. 19. Without any limitation being implied, in a specific embodiment, the DSC curve of crystalline form CS9 is substantially as depicted in FIG. 20, which shows two endothermic peaks and one exothermic peak. The first endothermic peak is at around 119° C. (onset temperature), the second endothermic peak is at 278° C. (onset temperature) and the exothermic peak is at around 191° C. (onset temperature).

Without any limitation being implied, in a specific embodiment, the TGA curve of crystalline form CS9 is substantially as depicted in FIG. 21, which shows about 10.1% weight loss when heated to 167° C.

According to the objective of the present disclosure, a process for preparing crystalline form CS9 of compound I is also provided. The process comprises: adding compound I in a solvent mixture comprising alcohols and toluene, stirring at room temperature, separating the solid, drying to obtain crystalline form CS9.

Preferably, said alcohol includes methanol.

According to another objective of the present disclosure, crystalline form CS3 of compound I is provided.

The X-ray powder diffraction pattern of crystalline form CS3 shows characteristic peaks at 2 theta values of 6.4°±0.2°, 15.0°±0.2° and 8.7°±0.2° using CuKα radiation. Furthermore, the X-ray powder diffraction pattern of crystalline form CS3 shows one or two characteristic peaks at 2 theta values of 13.1°±0.2° and 8.1°±0.2° using CuKα radiation. Preferably, the X-ray powder diffraction pattern of crystalline form CS3 shows two characteristic peaks at 2 theta values of 13.1°+0.2° and 8.1°+0.2° using CuKα radiation.

Furthermore, the X-ray powder diffraction pattern of crystalline form CS3 shows one or two or three characteristic peaks at 2 theta values of 7.2°+0.2°, 16.3°±0.2° and 10.4°±0.2° using CuKα radiation. Preferably, the X-ray powder diffraction pattern of crystalline form CS3 shows three characteristic peaks at 2 theta values of 7.2°±0.2°, 16.3°±0.2° and 10.4°±0.2° using CuKα radiation.

In a preferred embodiment, the X-ray powder diffraction pattern of crystalline form CS3 shows characteristic peaks at 2 theta values of 6.4°±0.2°, 15.0°±0.2°, 8.7°±0.2°, 13.1°±0.2°, 8.1°±0.2°, 7.2°±0.2°. 16.3°±0.2) and 10.4°±0.2° using CuKα radiation. Without any limitation being implied, in a specific embodiment, the X-ray powder diffraction pattern of crystalline form CS3 is substantially as depicted in FIG. 22. Without any limitation being implied, in a specific embodiment, the DSC curve of crystalline form CS3 is substantially as depicted in FIG. 23, which shows one endothermic peak and one exothermic peak. The exothermic peak is at around 178° C. (onset temperature) and the endothermic peak is at around 276° C. (onset temperature). Without any limitation being implied, in a specific embodiment, the TGA curve of crystalline form CS3 is substantially as depicted in FIG. 24, which shows about 5.5% weight loss when heated to 197° C.

According to the objective of the present disclosure, a process for preparing crystalline form CS3 of compound I is also provided. The process comprises: adding the solid of compound I into a solvent mixture comprising ethers and halohydrocarbons, stirring at 50° C., isolating the solid and drying to obtain crystalline form CS3.

Preferably, said ether is tetrahydrofuran, said halohydrocarbon is dichloromethane. Crystalline form CS3 of compound I. of the present disclosure has the following advantages:

1. Good stability. Crystalline form CS3 of compound I of the present disclosure is stable for at least 5 months under the conditions of 25° C./60% RH and 40° C./75% RH. Crystalline form and chemical purity remain substantially unchanged during storage. A better stability of crystalline form CS3 of compound I can reduce the risk of drug dissolution rate and bioavailability change due to the change of crystalline forms, which is of great significance to ensure the efficacy and safety of drugs and prevent adverse drug reactions. Crystalline form CS3 of compound I with better stability is controllable during the crystallization, formulation and storage process and not easy to produce mixed crystal, which is of great value for industrial production, 2. High solubility. When prepared into saturated solutions in FeSSIF (Fed state simulated intestinal fluids, pH-5.0) and FaSSIF (Fasted state simulated intestinal pH=6.5), crystalline form CS3 of compound I of the present disclosure has 4-11 times higher solubility than Form A of CN105849100A in FeSSIF and 6-16 times higher solubility than Form A of CN105849100A in FaSSIF at 1 h, 4 h and 24 h time point. Higher kinetic solubility of crystalline form CS3 of compound I can ensure the disintegration and absorption of the drug in the stomach and intestine of the human body, thereby improving the drug effect and increasing the blood drug concentration, which can effectively improve the bioavailability of the drug products. According to the objective of the present disclosure, a pharmaceutical composition is provided, said pharmaceutical composition comprises a therapeutically effective amount of crystalline form CS3 of compound I and pharmaceutically acceptable carriers, diluents or excipients.

Furthermore, crystalline form CS3 of compound I can be used for preparing drugs inhibiting virus protein.

Furthermore, crystalline form CS3 of compound I can be used for preparing drugs treating influenza A.

Said "room temperature" of the present disclosure refers to 10-30° C.

Said "isomorphotropism", also known as isomorphism, refer to similarity or sameness in the crystal structure of similar chemical compositions under the same thermodynamic condition.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, hydrochloride Form CS1, hydrochloride Form CS2, hydrochloride Form CS3, hydrochloride Form CS4, crystalline form CS3 of compound I and crystalline form CS9 of compound I of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

DETAILED DESCRIPTION

Figure 1:
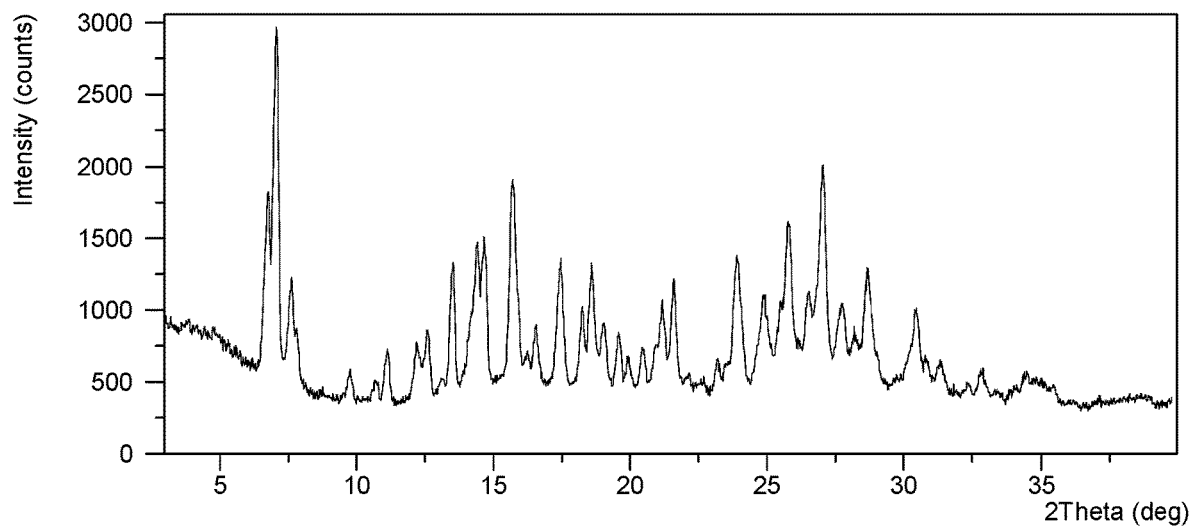
FIG. 1 shows an XRPD pattern of hydrochloride Form CS3 according to example 10 of the present disclosure.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

Instruments and Methods Used for Data Collection

X-ray powder diffraction patterns in the present disclosure were acquired by a Bruker D2 PHASER X-ray powder diffractometer. The parameters of the X-ray powder diffraction method of the present disclosure were as follows:

X-ray Reflection: Cu, Kα,

Kα1 (Å): 1.54060; Kα2 (Å): 1.54439

Kα2/Kα1 intensity ratio: 0.50
Voltage: 30 (kV)
Current: 10 (mA)
Scan range: from 3.0 degree to 40.0 degree Differential scanning calorimetry (DSC) data in the present disclosure were acquired by a TA Q2000. The instrument control software is Thermal Advantage and the analysis software is Universal Analysis. Generally, 1-10 mg of the sample is put in the crimped aluminum crucible (unless otherwise specified), and heated from room temperature to the set temperature wider the protection of dry $N_2$ with a heating rate of 10° C./min. The TA software records the heat flow of the sample during the heating process. In the present disclosure, the melting point is reported as the onset temperature.

Thermal gravimetric analysis (TGA) data in the present disclosure were acquired by a TA Q500. The instrument control software is Thermal Advantage and the analysis software is Universal Analysis. Generally, 5-15 mg of the sample is placed in the platinum crucible, and heated from room temperature to the set temperature under the protection of 50 mL/min dry $N_2$ with a heating rate of 10° C./min by the method of segmented high-resolution detection. The TA software records the weight change of the sample during the heating process. The water content of the crystalline form of the present disclosure is calculated based on the TGA weight loss. As is known to those skilled in the art, TGA weight loss is a reference for the water content of the crystalline form, but not absolutely represent the number of water molecules in the crystalline form.

Dynamic Vapor Sorption (DVS) was measured via a SMS (Surface Measurement Systems Ltd.) intrinsic DVS instrument. Its control software is DVS-Intrinsic control software, and its analysis software is DVS-Intrinsic Analysis software. Typical Parameters for DVS test are as follows:
Temperature: 25° C.
Gas and flow rate: $N_2$, 200 mL/min
dm/dt: 0.002%/min
RH range: 0% RH to 95% RH Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Unless otherwise specified, the following examples were conducted at room temperature.

Raw materials of compound I and/or a salt thereof used in the following examples were prepared by known methods in the prior art, for example, the method disclosed in CN105849100A.

DETAILED DESCRIPTION

Example 1-5 Preparation of Hydrochloride Form CS1

As shown in Table 1, certain amount of VX-787 solid was weighted and added into corresponding volume of acetic acid. These solutions were stirred at room temperature for 30-60 minutes, and then a certain amount of 12 mol/L concentrated hydrochloric acid solution was added to the solutions. The obtained suspensions were stirred at room temperature for 1-2 days, and the solid was obtained by centrifuging and vacuum drying at room temperature. The solids obtained in the examples in Table 1 were labeled as samples 1-5.

TABLE 1

| Example | Amount (mg) | Volume of acetic acid (mL) | Volume of hydrochloric acid (mL) | Label |
|---|---|---|---|---|
| 1 | 500.3 | 9.0 | 0.1 | Sample 1 |
| 2 | 10.2 | 0.5 | 0.002 | Sample 2 |
| 3 | 20.1 | 0.5 | 0.004 | Sample 3 |
| 4 | 99.8 | 2.0 | 0.02 | Sample 4 |
| 5 | 499.9 | 8.0 | 0.108 | Sample 5 |

Samples 1-5 were confirmed to be hydrochloride Form CS1 by XRPD.

Figure 4:
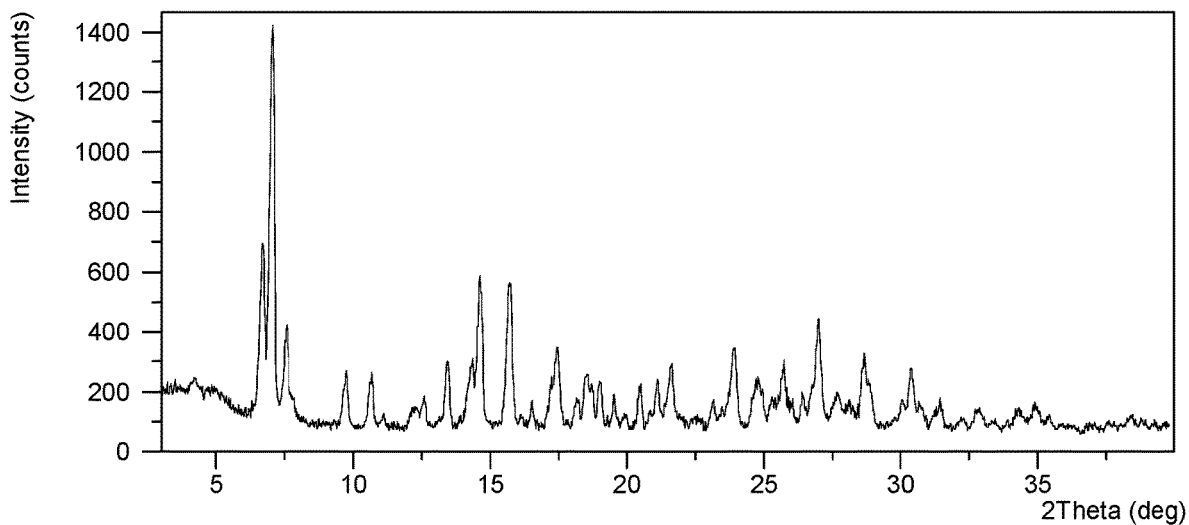
FIG. 4 shows an XRPD pattern of hydrochloride Form CS1 according to example 1 of the present disclosure.
Figure 5:
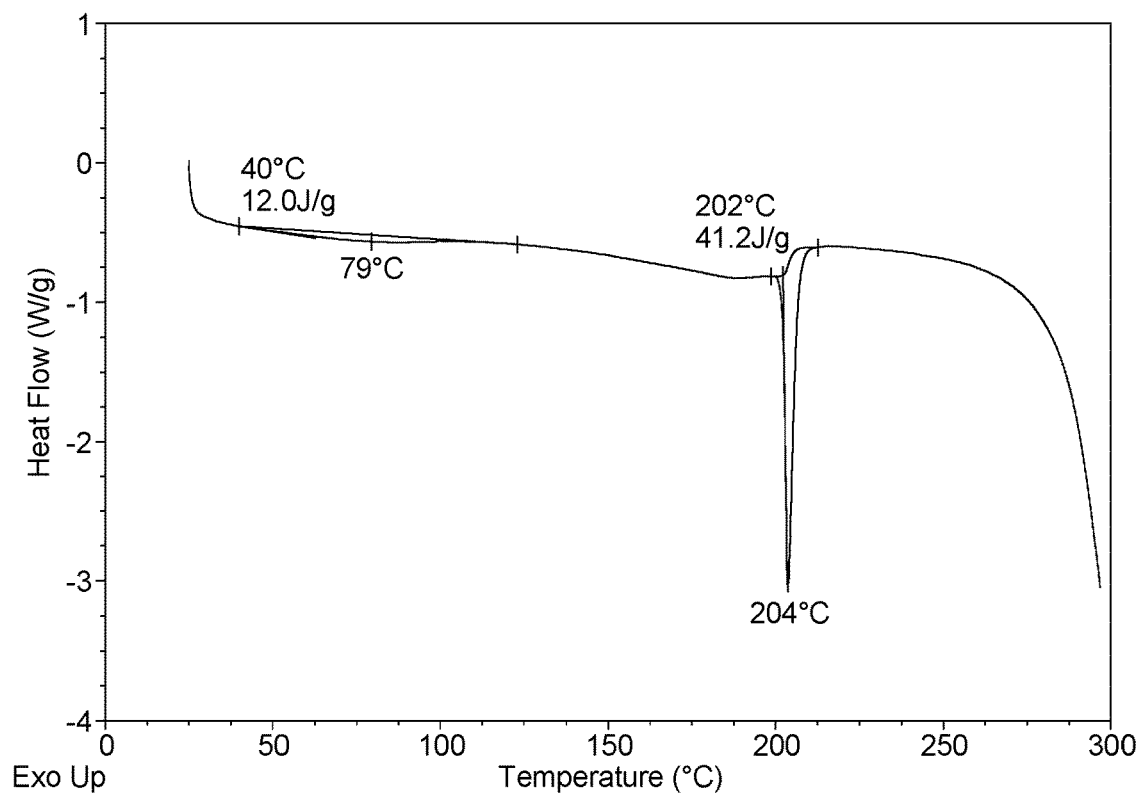
FIG. 5 shows a DSC curve of hydrochloride Form CS1 according to example 1 of the present disclosure.
Figure 6:
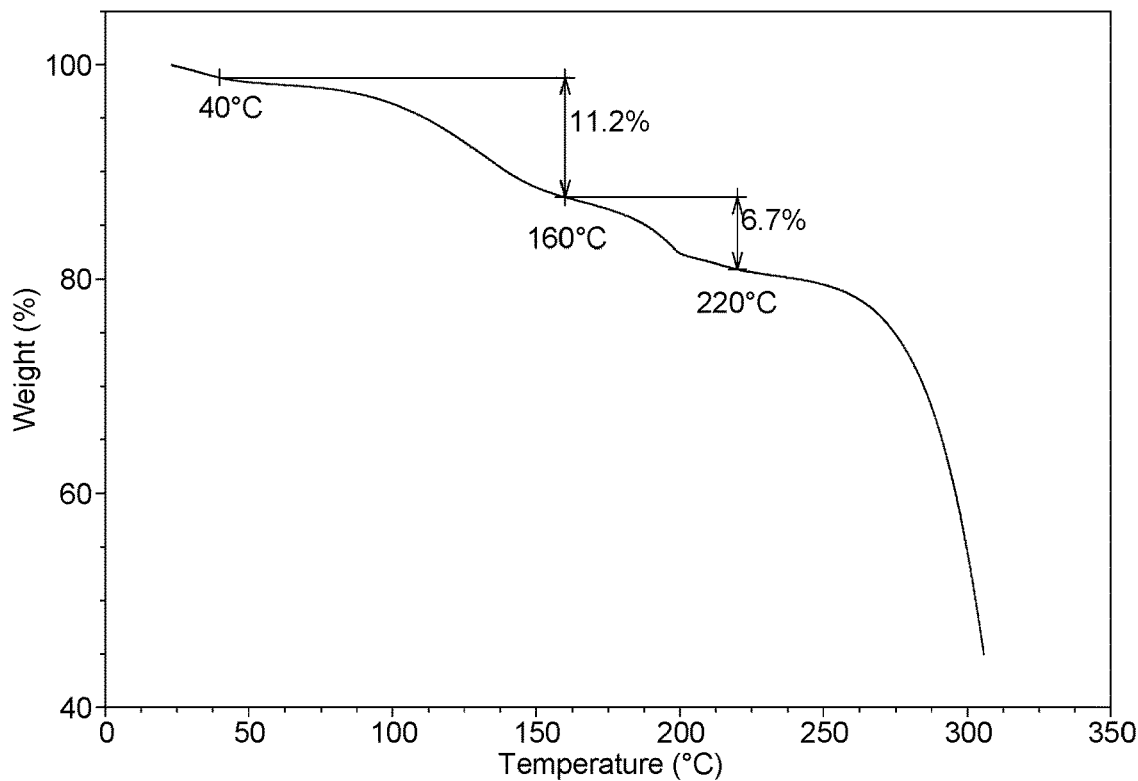
FIG. 6 shows a TGA curve of hydrochloride Form CS1 according to example 1 of the present disclosure

Sample 1 was selected for further characterization. The XRPD pattern is substantially as depicted in FIG. 4, and the XRPD data are listed in Table 2. The DSC curve is substantially as depicted in FIG. 5, which shows two endothermic peaks. The first endothermic peak is at around 40° C. and the second endothermic peak is at around 202° C. The TGA curve is substantially as depicted in FIG. 6, which shows about 11.2% weight loss when heated to 160° C. Each mole of VX-787 hydrochloride Form CS1 was calculated to contain about 1 mole of acetic acid according to the TGA data. When heating to 220° C., about 6.7% weight loss was observed.

Figure 14:
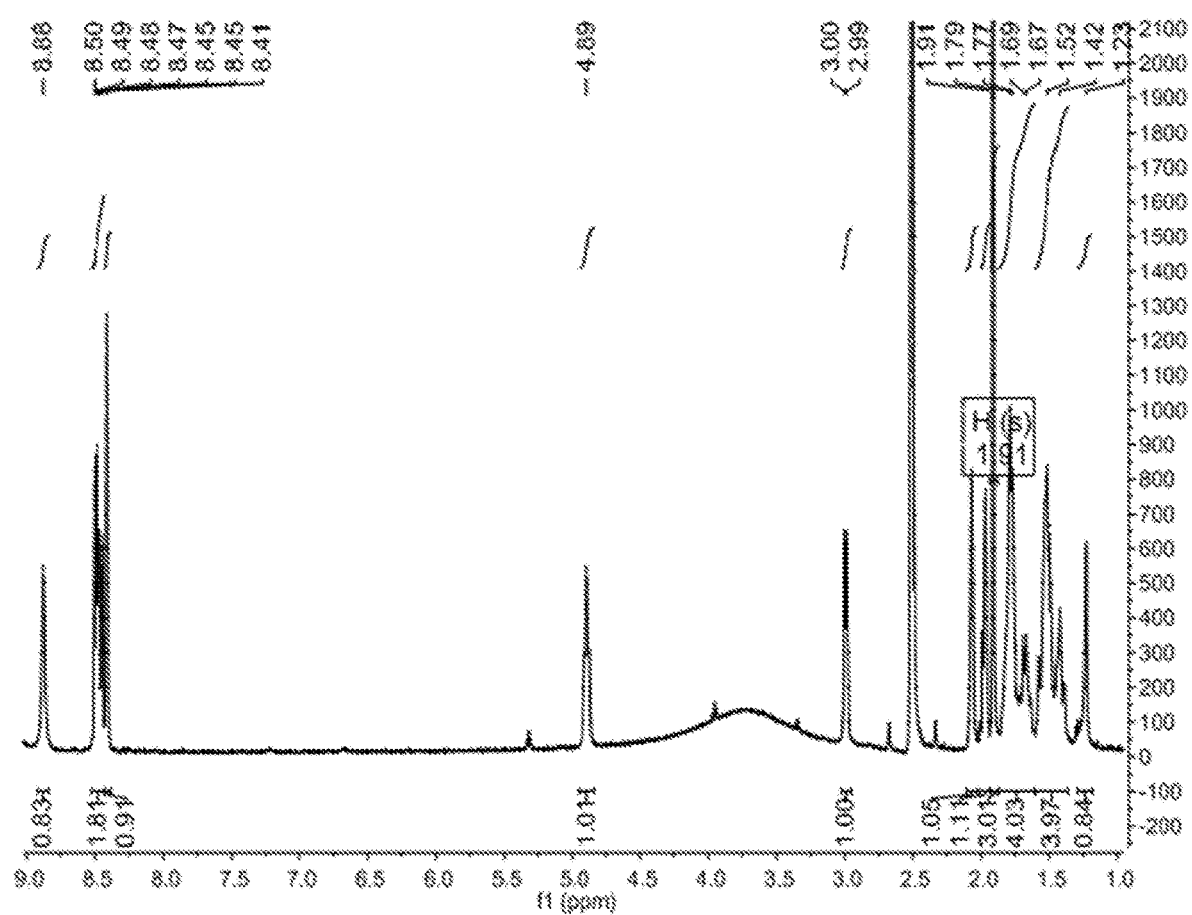
FIG. 14 shows a $^1$H NMR spectrum of hydrochloride Form CS1

The hydrochloride Form CS1 shows a singlet peak at 1.91 ppm, corresponding to the chemical shift of methyl protons of the acetic acid ($CH_3COOH$). According to the $^1$H NMR data, the molar ratio of the acetic acid molecule to the API is calculated to be 1:1. The $^1$H NMR spectrum of hydrochloride Form CS1 is substantially as depicted in FIG. 14, and the corresponding data are: $^1$H NMR. (400 MHz, DMSO) δ 8.88 (s, 1H), 8.53-8.43 (s, 2H), 8.41 (in, 1H), 4.89 (m, 1H), 2.99 (d, J=6.2 Hz, 1H), 2.08 (d, J=5.9 Hz, 1H), 1.98 (d, J=8.6 Hz, 1H), 1.91 (s, 3H), 1.86-1.61 (m, 4H), 1.48 (dd, J=54.1, 17.6 Hz, 4H), 1.23 (s, 1H).

TABLE 2

| 2θ | d spacing | Intensity % |
|---|---|---|
| 6.69 | 13.20 | 43.73 |
| 7.06 | 12.52 | 100.00 |
| 7.58 | 11.67 | 24.03 |
| 9.76 | 9.06 | 13.63 |
| 10.70 | 8.2 | 13.63 |
| 11.11 | 7.96 | 2.39 |
| 12.18 | 7.27 | 3.85 |
| 12.60 | 7.03 | 7.59 |
| 13.46 | 6.58 | 15.57 |
| 14.29 | 6.20 | 14.58 |
| 14.62 | 6.06 | 38.38 |
| 15.73 | 5.64 | 36.30 |
| 16.53 | 5.36 | 6.29 |
| 17.44 | 5.08 | 20.34 |
| 18.18 | 4.88 | 6.53 |
| 18.53 | 4.79 | 13.11 |
| 18.73 | 4.74 | 9.94 |
| 19.02 | 4.67 | 11.49 |
| 19.53 | 4.55 | 8.30 |
| 19.96 | 4.45 | 2.90 |
| 20.48 | 4.34 | 9.95 |
| 21.12 | 4.21 | 11.97 |
| 21.62 | 4.11 | 15.43 |
| 22.52 | 3.95 | 2.44 |
| 23.14 | 3.84 | 6.61 |
| 23.91 | 3.72 | 20.03 |
| 24.77 | 3.59 | 12.02 |
| 25.71 | 3.47 | 16.15 |
| 26.03 | 3.42 | 6.73 |
| 26.41 | 3.37 | 8.07 |
| 26.99 | 3.30 | 28.01 |
| 27.67 | 3.22 | 8.39 |

TABLE 2-continued

| 2θ | d spacing | Intensity % |
|---|---|---|
| 28.65 | 3.12 | 16.41 |
| 28.91 | 3.09 | 9.81 |
| 30.07 | 2.97 | 6.88 |
| 30.38 | 2.94 | 15.03 |
| 31.44 | 2.85 | 6.39 |
| 32.22 | 2.78 | 1.89 |
| 32.80 | 2.73 | 4.30 |
| 33.39 | 2.68 | 1.14 |
| 34.30 | 2.61 | 4.78 |
| 34.90 | 2.57 | 5.42 |
| 38.39 | 2.34 | 2.63 |

Example 6 Preparation of Hydrochloride Form CS1

Figure 17:
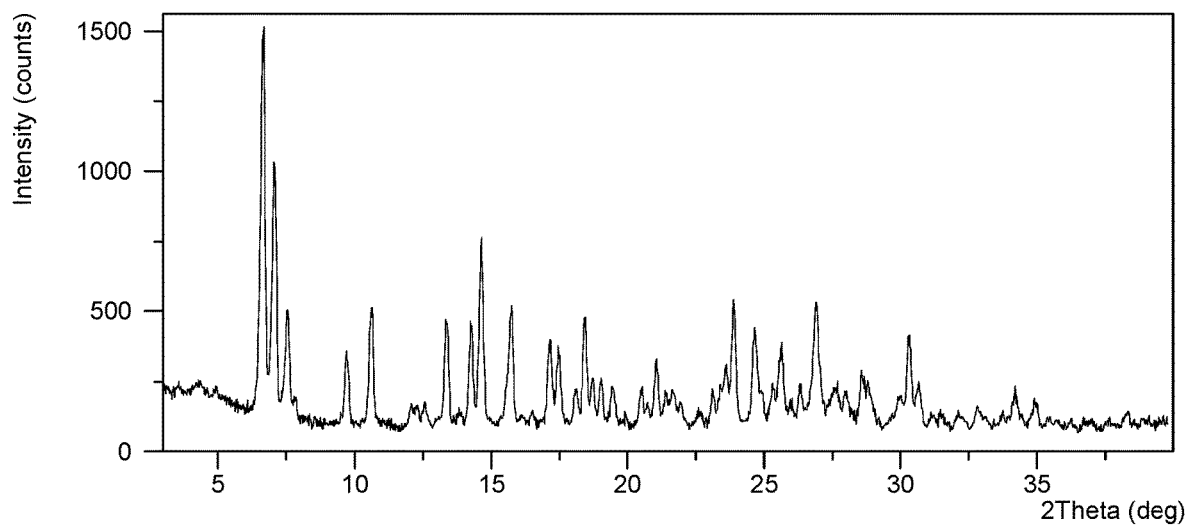
FIG. 17 shows an XRPD pattern of hydrochloride Form CS1 according to example 6 of the present disclosure

149.6 mg of VX-787 hydrochloride solid was weighed into a 5-mL glass vial followed by adding about 1 mL of acetic acid. The suspension was stirred at room temperature (about 25° C.) for 1 day, then centrifuged and dried under vacuum at room temperature. The solid obtained in this example was confirmed to be hydrochloride Form CS1, and the XRPD pattern is substantially as depicted in FIG. 17 and Table 3.

TABLE 3

| 2θ | d spacing | Intensity % |
|---|---|---|
| 6.66 | 13.28 | 100.00 |
| 7.06 | 1.51 | 66.67 |
| 7.54 | 11.72 | 28.12 |
| 7.83 | 11.29 | 4.43 |
| 9.72 | 9.10 | 17.9 |
| 10.64 | 8.32 | 30.64 |
| 12.09 | 7.32 | 4.90 |
| 12.57 | 7.04 | 5.62 |
| 13.37 | 6.62 | 26.59 |
| 14.28 | 6.20 | 25.71 |
| 14.65 | 6.05 | 49.57 |
| 15.74 | 5.63 | 30.45 |
| 16.51 | 5.37 | 3.42 |
| 17.15 | 5.17 | 22.26 |
| 17.47 | 5.08 | 18.88 |
| 18.09 | 4.90 | 9.42 |
| 18.45 | 4.81 | 28.53 |
| 18.73 | 4.74 | 12.40 |
| 19.04 | 4.66 | 12.30 |
| 19.46 | 4.56 | 9.93 |
| 20.51 | 4.33 | 9.38 |
| 21.06 | 4.22 | 17.31 |
| 21.42 | 4.15 | 9.11 |
| 21.67 | 4.10 | 8.96 |
| 21.94 | 4.05 | 6.25 |
| 22.64 | 3.93 | 3.15 |
| 23.13 | 3.85 | 8.17 |
| 23.60 | 3.77 | 16.12 |
| 23.88 | 3.73 | 33.15 |
| 24.65 | 3.61 | 25.85 |
| 25.32 | 3.52 | 10.73 |
| 25.63 | 3.48 | 20.02 |
| 25.97 | 3.43 | 6.13 |
| 26.32 | 3.39 | 11.29 |
| 26.90 | 3.31 | 32.36 |
| 27.61 | 3.23 | 9.20 |
| 27.98 | 3.19 | 8.69 |
| 28.56 | 3.13 | 14.24 |
| 29.97 | 2.98 | 7.47 |
| 30.31 | 2.95 | 23.75 |
| 30.67 | 2.92 | 10.95 |
| 31.17 | 2.87 | 2.44 |
| 31.48 | 2.84 | 2.88 |
| 32.10 | 2.79 | 3.13 |
| 32.82 | 2.73 | 4.96 |
| 33.72 | 2.66 | 3.71 |

TABLE 3-continued

| 2θ | d spacing | Intensity % |
|---|---|---|
| 34.19 | 2.62 | 9.14 |
| 34.93 | 2.57 | 6.22 |
| 35.41 | 2.53 | 1.74 |

Example 7 Stability of Hydrochloride Form CS1

The hydrochloride Form CS1 prepared by the present disclosure was stored under 25° C./60% RH and 40° C./75% RH for 1 month. The crystalline forms were checked by XRPD before and after storing. The results are shown in Table 4.

TABLE 4

| Initial crystalline form | Condition | Time | Change of crystalline form |
|---|---|---|---|
| Hydrochloride Form CS1 | 25° C./60% RH | One month | Unchanged |
| Hydrochloride Form CS1 | 40° C./75% RH | One month | Unchanged |

The results show that hydrochloride Form CS1 keeps stable for at least 1 month at 25° C./60% RH and 40° C./75% RH. The crystalline form remains unchanged. The purities remain substantially unchanged, and the purities of both samples are maintained to be above 98%. It can be seen that hydrochloride Form CS1 provided by the present disclosure has good stability.

Example 8 Mechanical Stability of Hydrochloride Form CS1

Figure 25:
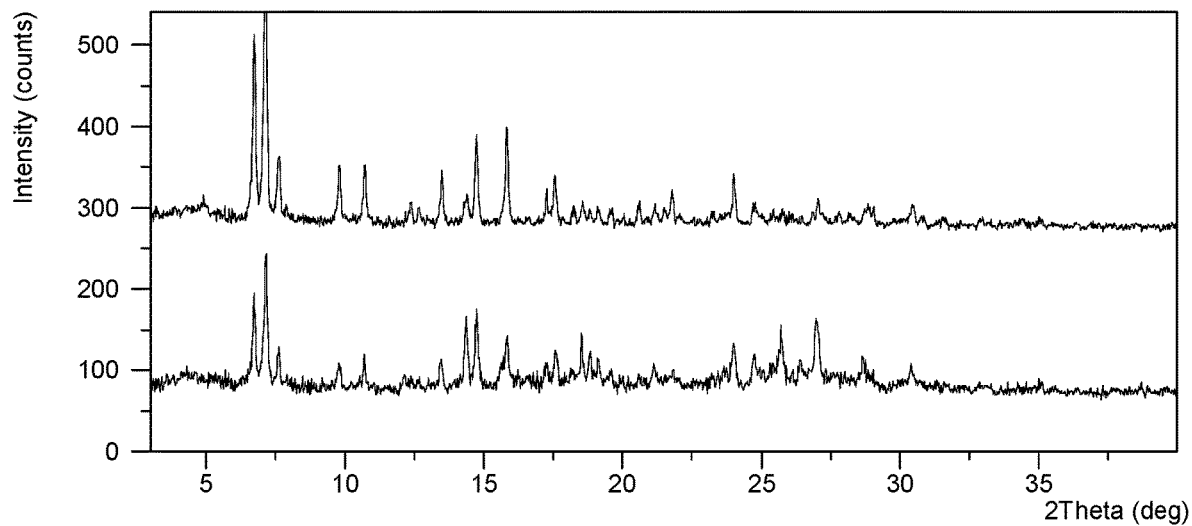
FIG. 25 shows an XRPD pattern overlay of hydrochloride Form CS1 before and after grinding (top: XRPD pattern before grinding, bottom: XRPD pattern after grinding).

About 10 mg of hydrochloride Form CS1 of the present disclosure was taken and ground in an agate mortar for about 2 minutes. The XRPD result is shown in FIG. 25. The result shows that no form change is observed of hydrochloride Form CS1 before and after grinding.

Example 9 Preparation of Hydrochloride Form CS2

Figure 7:
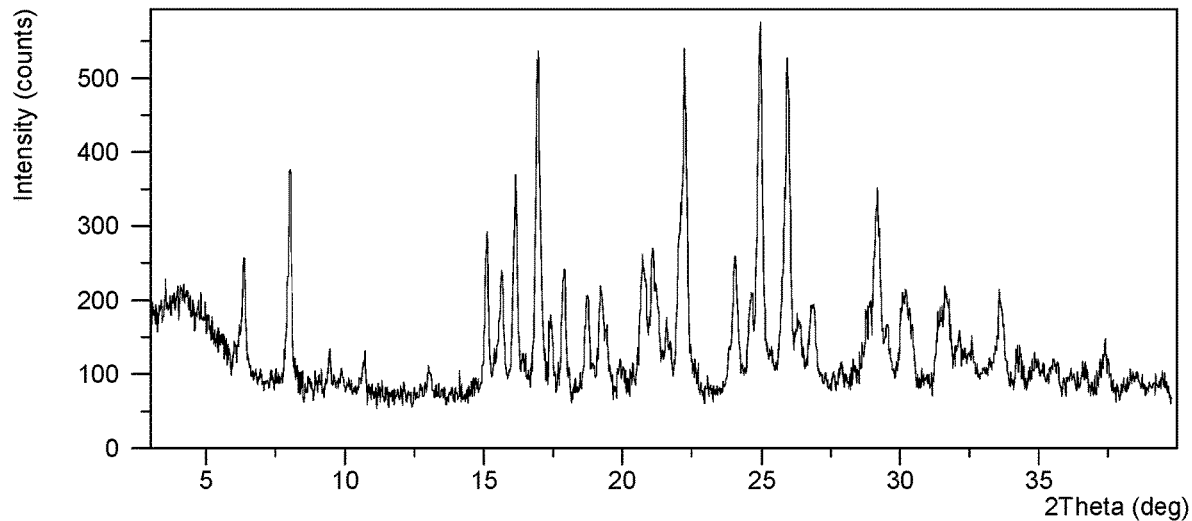
FIG. 7 shows an XRPD pattern of hydrochloride Form CS2 according to example 9 of the present disclosure.

99.7 mg of VX-787 solid was weighed into a 5-mL glass vial. 1.5 mL of chloroform was added. The sample was stirred at room temperature (about 25° C.) for 30 minutes. 0.02 mL of 12 mol/L concentrated hydrochloric acid was added into the above solution. The sample was stirred at room temperature for 12 hours. The solid was obtained by centrifuging and vacuum drying at room temperature. The solid obtained in this example was confirmed to be hydrochloride Form CS2, and the XRPD pattern is substantially as depicted in FIG. 7 and Table 5.

Figure 15:
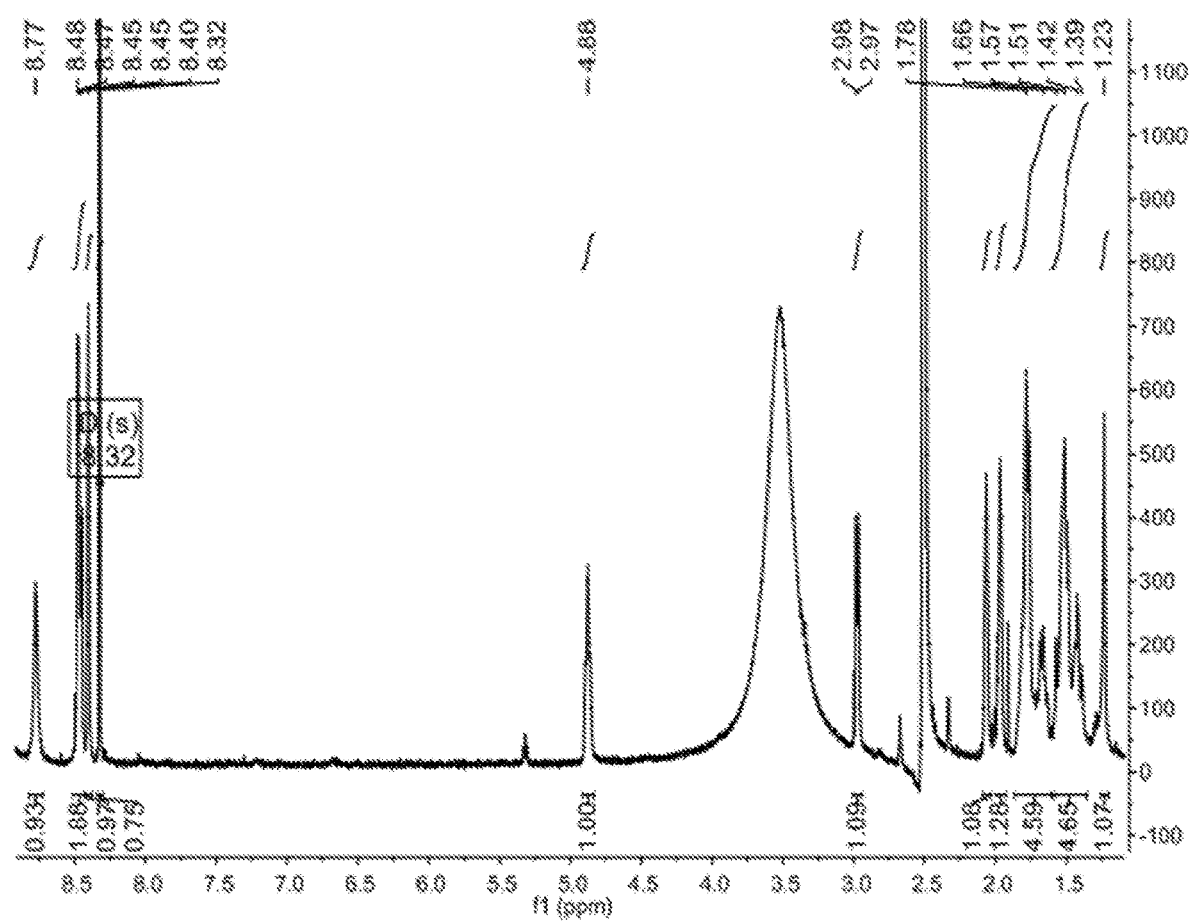
FIG. 15 shows a $^1$H NMR spectrum of hydrochloride Form CS2

Hydrochloride Form CS2 shows a singlet peak at 8.32 ppm, corresponding to the chemical shift of protons of chloroform ($CHCl_3$). According to the $^1H$ NMR data, the molar ratio of chloroform to compound I is 0.75:1. The $^1H$ NMR spectrum of hydrochloride Form CS2 is substantially as depicted in FIG. 15, and the corresponding data are: {$^1H$ NMR (400 MHz, DMSO) δ 8.77 (s, 1H), 8.46 (dd, J=9.5, 3.1 Hz, 2H), 8.40 (m, 1H), 8.32 (s, 0.75H), 4.88 (m, 1H), 2.98 (d, J=6.3 Hz, 1H), 2.06 (d, 1H), 1.97 (d, 1H), 1.72 (dd, J=41.6, 7.4 Hz, 4H), 1.47 (dd, J=54.7, 17.4 Hz, 4H), 1.23 (s, 1H)}.

TABLE 5

| 2θ | d spacing | Intensity % |
|---|---|---|
| 6.36 | 13.90 | 30.63 |
| 8.02 | 11.02 | 57.90 |
| 9.45 | 9.36 | 8.50 |
| 10.72 | 8.26 | 8.65 |
| 13.05 | 6.79 | 6.96 |
| 15.11 | 5.86 | 41.67 |
| 15.65 | 5.66 | 34.01 |
| 16.15 | 5.49 | 60.14 |
| 16.95 | 5.23 | 86.59 |
| 17.41 | 5.10 | 19.79 |
| 17.89 | 4.96 | 34.10 |
| 18.75 | 4.73 | 26.63 |
| 19.22 | 4.62 | 29.22 |
| 19.91 | 4.46 | 8.36 |
| 20.74 | 4.28 | 35.37 |
| 21.10 | 4.21 | 38.89 |
| 21.61 | 4.11 | 18.53 |
| 22.25 | 4.00 | 94.29 |
| 24.05 | 3.70 | 37.37 |
| 24.59 | 3.62 | 24.42 |
| 24.95 | 3.57 | 100.00 |
| 25.94 | 3.43 | 83.09 |
| 26.33 | 3.38 | 19.56 |
| 26.84 | 3.32 | 23.69 |
| 29.19 | 3.06 | 55.34 |
| 30.17 | 2.96 | 25.13 |
| 31.37 | 2.85 | 18.64 |
| 31.67 | 2.83 | 25.95 |
| 33.59 | 2.67 | 26.86 |
| 34.26 | 2.62 | 8.68 |
| 34.88 | 2.57 | 7.90 |
| 35.55 | 2.53 | 7.31 |
| 37.38 | 2.41 | 11.90 |
| 38.42 | 2.34 | 3.56 |

Figure 8:
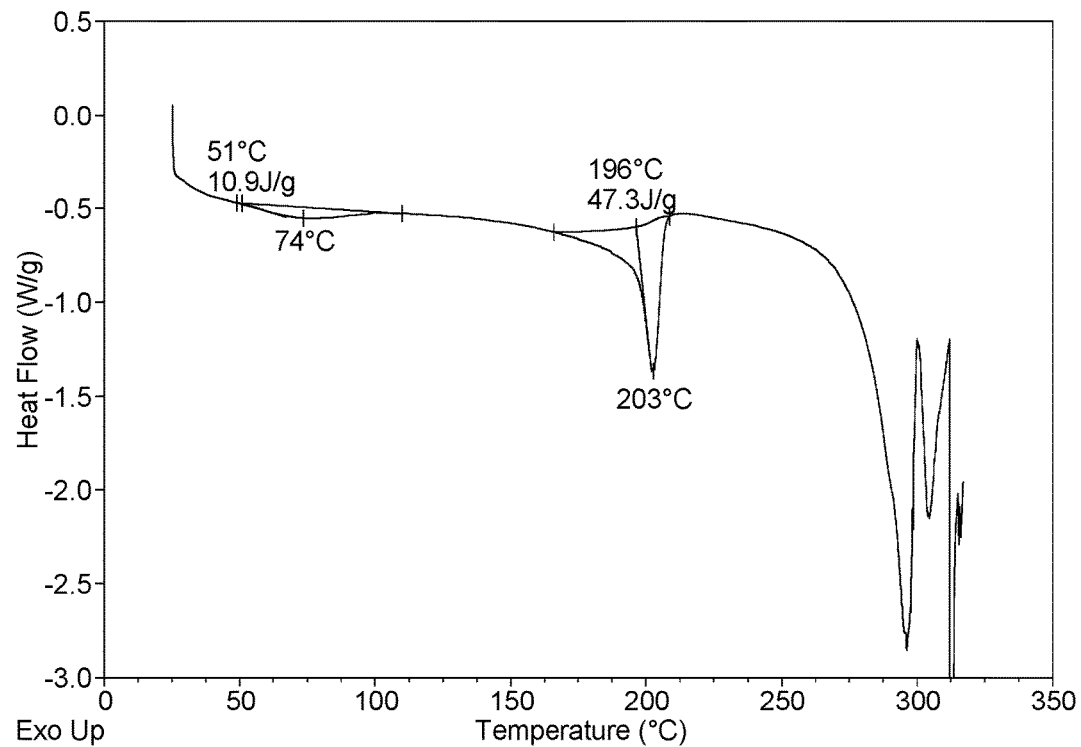
FIG. 8 shows a DSC curve of hydrochloride Form CS2 according to example 9 of the present disclosure.

The DSC curve is substantially as depicted in FIG. 8, which shows two endothermic peaks. The first endothermic peak starts to appear at around 51° C., which is caused by the loss of chloroform at around this temperature ($^1$H NMR data showed the presence of chloroform in the compound, as shown in FIG. 15), the second endothermic peak is at around 196° C.

Figure 9:
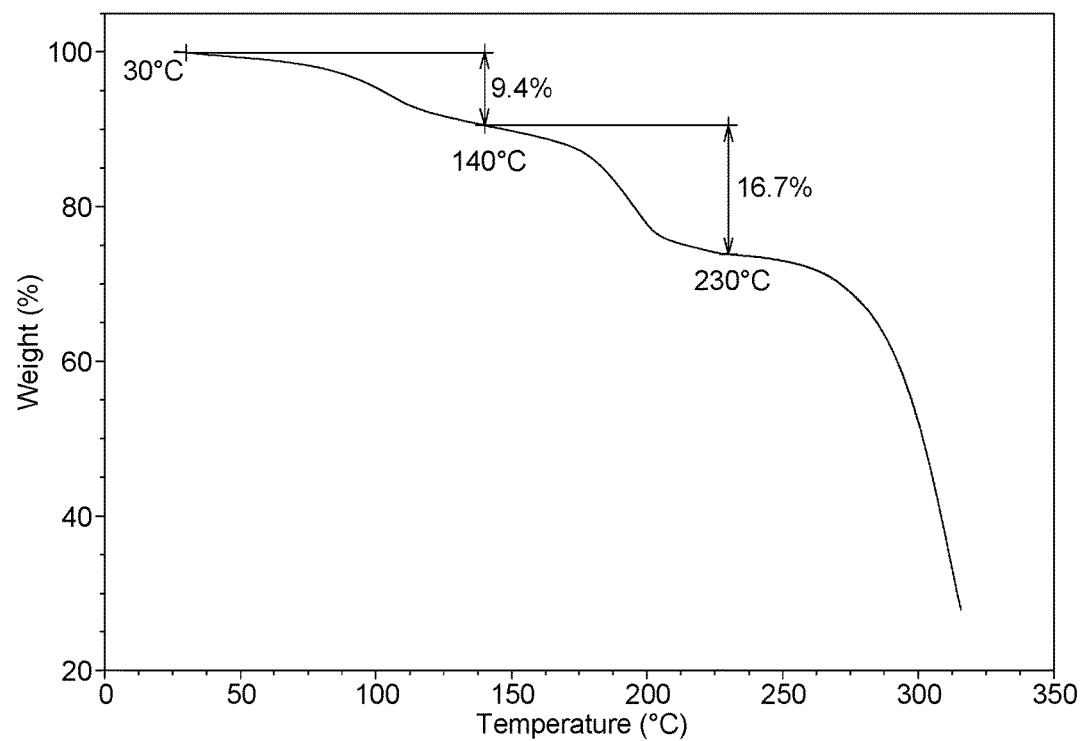
FIG. 9 shows a TGA curve of hydrochloride Form CS2 according to example 9 of the present disclosure

The TGA curve of hydrochloride Form CS2 is substantially as depicted in FIG. 9, which shows about 9.4% weight loss when heating to 140° C. When heated to 230° C., about 16.7% weight loss is observed. About 0.75 mole of chloroform is calculated to be contained in each mole of VX-787 hydrochloride Form CS2.

Example 10 Preparation of Hydrochloride Form CS3

About 10 mg of VX-787 hydrochloride Form CS1 was weighed and heated by TGA. The sample was heated from room temperature (about 25° C.) to 150° C.; at 10° C./min under nitrogen protection, and held stable at 150° C. for 10 minutes. Then the sample was transferred to room temperature. The solid obtained in this example was confirmed to be hydrochloride Form CS3, and the XRPD data is substantially as depicted in FIG. 1 and Table 6,

TABLE 6

| 2θ | d spacing | Intensity % |
|---|---|---|
| 6.76 | 13.07 | 50.90 |
| 7.07 | 12.50 | 100.00 |
| 7.64 | 11.58 | 29.97 |
| 7.83 | 11.29 | 15.37 |
| 9.77 | 9.05 | 8.27 |
| 10.73 | 8.24 | 4.81 |
| 11.15 | 7.94 | 13.40 |
| 12.22 | 7.24 | 15.73 |
| 12.59 | 7.03 | 20.09 |
| 13.13 | 6.74 | 5.94 |
| 13.53 | 6.55 | 39.07 |
| 14.41 | 6.15 | 44.54 |
| 14.67 | 6.04 | 46.31 |
| 15.71 | 5.64 | 62.63 |
| 16.55 | 5.36 | 21.64 |
| 17.45 | 5.08 | 40.72 |
| 18.26 | 4.86 | 27.27 |
| 18.61 | 4.77 | 37.66 |
| 19.05 | 4.66 | 22.61 |
| 19.59 | 4.53 | 19.55 |
| 19.93 | 4.45 | 12.83 |
| 20.46 | 4.34 | 14.55 |
| 21.18 | 4.20 | 29.16 |
| 21.60 | 4.11 | 35.08 |
| 22.11 | 4.02 | 7.43 |
| 23.20 | 3.83 | 11.50 |
| 23.91 | 3.72 | 41.92 |
| 24.88 | 3.58 | 29.78 |
| 25.78 | 3.46 | 50.74 |
| 26.51 | 3.36 | 31.79 |
| 27.03 | 3.30 | 68.58 |
| 27.73 | 3.22 | 28.20 |
| 28.19 | 3.17 | 19.89 |
| 28.67 | 3.11 | 38.80 |
| 30.43 | 2.94 | 26.16 |
| 30.82 | 2.90 | 12.66 |
| 31.32 | 2.86 | 11.71 |
| 32.35 | 2.77 | 5.90 |
| 32.83 | 2.73 | 9.26 |
| 34.46 | 2.60 | 8.43 |
| 35.44 | 2.53 | 5.41 |

Figure 13:
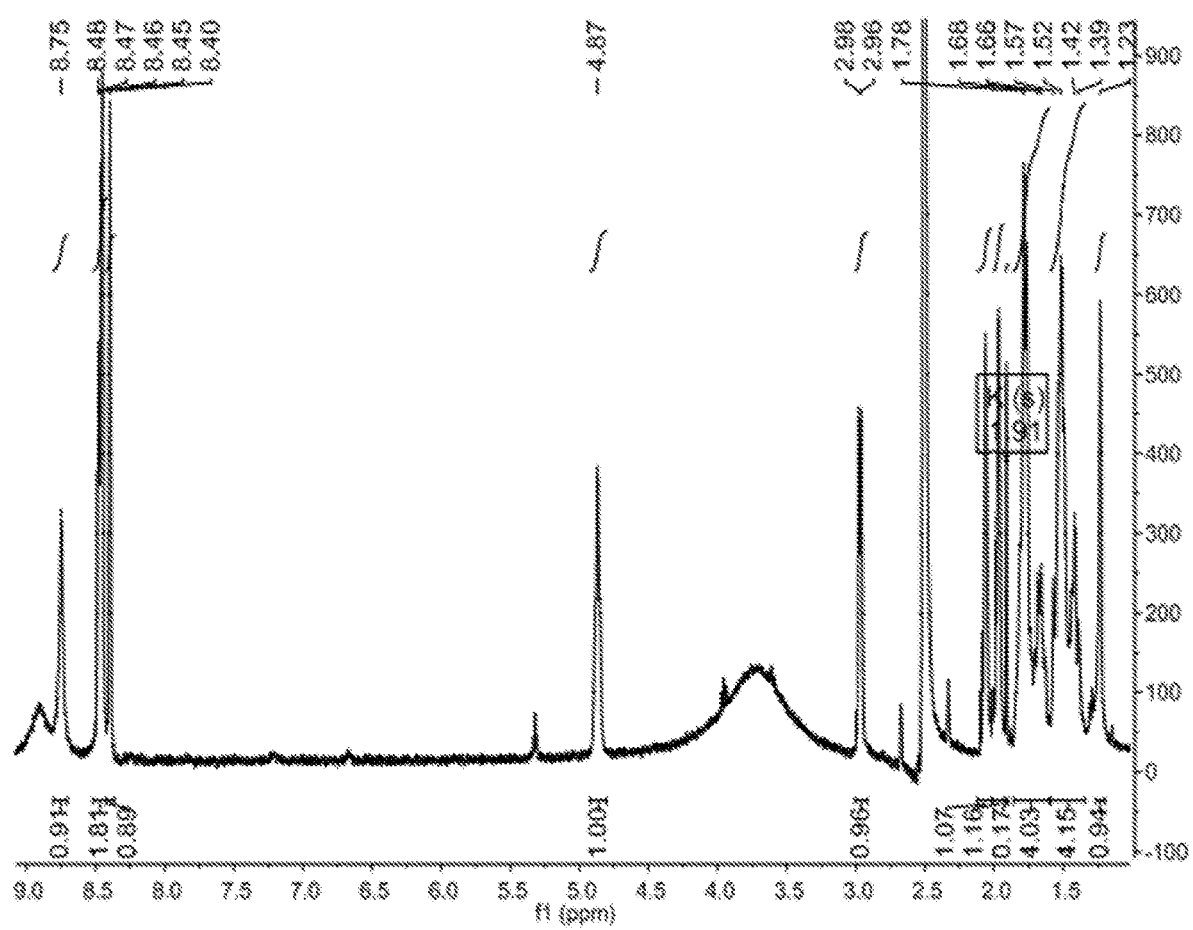
FIG. 13 shows a $^1$H NMR spectrum of hydrochloride Form CS3

The NMR spectrum of hydrochloride Form CS3 is substantially as depicted in FIG. 13, and the corresponding data are: {$^1$H NMR (400 MHz, DMSO) δ 8.75 (s, 1H), 8.46 (dd, J=9.4, 2.8 Hz, 2H), 8.40 (m, 1H), 4.87 (m, 1H), 2.97 (d, J=6.7 Hz, 1H), 2.09-2.02 (m, 1H), 1.98 (d, J=8.6 Hz, 1H), 1.91 (s, 0.17H). 1.72 (dd, J=41.1, 9.0 Hz, 4H), 1.47 (dd, J=55, 8, 16.5 Hz, 4H), 1.23 (s, 1H)}.

Figure 2:
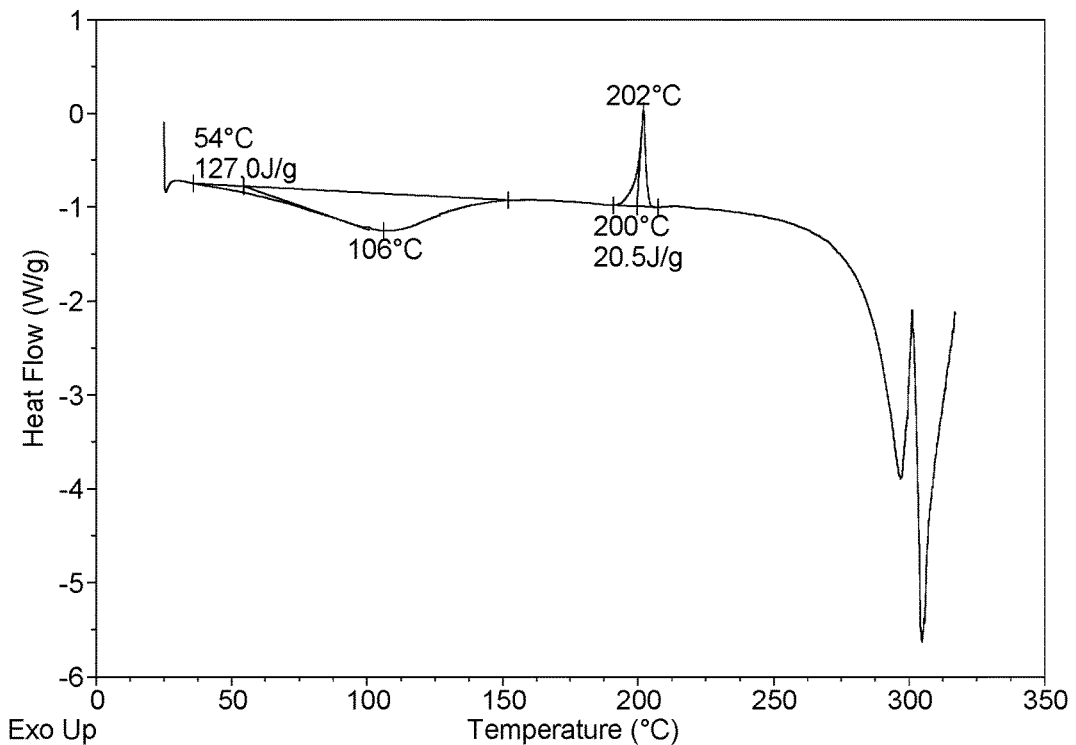
FIG. 2 shows a DSC curve of hydrochloride Form CS3 according to example 10 of the present disclosure.
Figure 3:
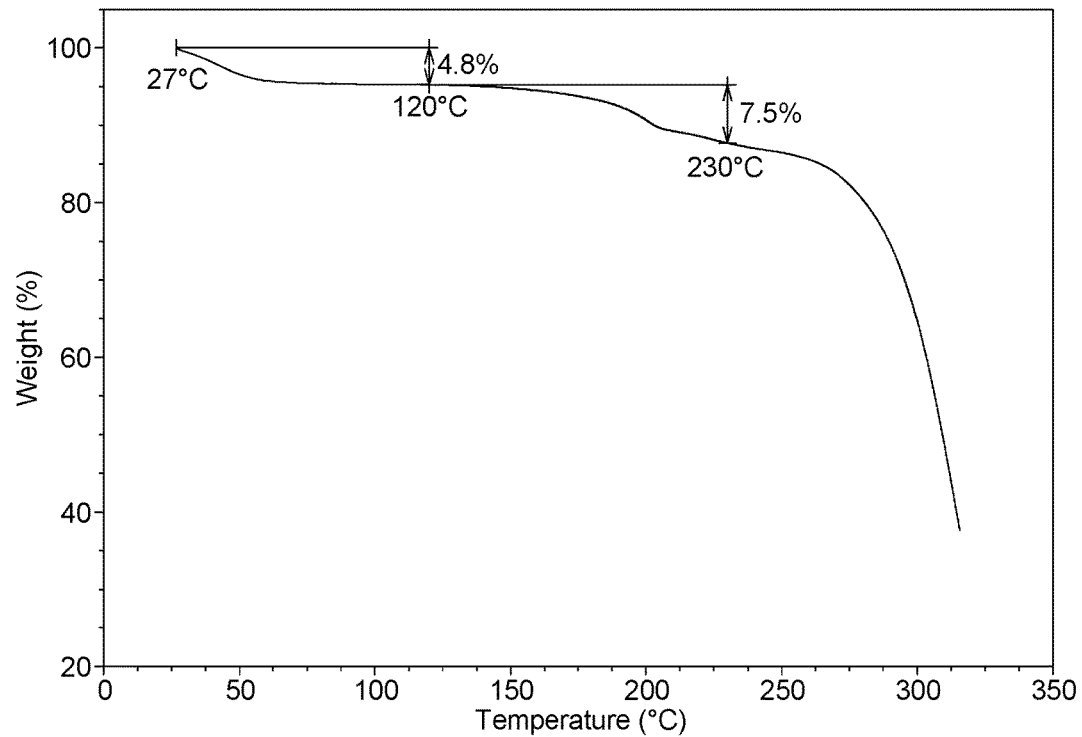
FIG. 3 shows a TGA curve of hydrochloride Form CS3 according to example 10 of the present disclosure.

The DSC curve of this crystalline form is substantially as depicted in FIG. 2, which shows an endothermic peak and an exothermic peak. The endothermic peak starts to appear at around 54° C., and the exothermic peak starts to appear at around 200° C. The TGA curve of this crystalline form is substantially as depicted in FIG. 3, which shows about 4.8% weight loss when heating to 120° C., and about 7.5% weight loss when further heated to 230° C.

Example 11 Dynamic Solubility Comparison of Hydrochloride Form CS3 and Hydrochloride Form A in CN1058491100A 12 mg of hydrochloride Form CS3 prepared in the present disclosure and the hydrochloride Form A in CN105849100A were accurately weighed and placed in vials, followed by adding 1.2 mL of water. The samples were rotated at 30 rpm on a rotator and sampled at 1 hour, 4 hours, and 24 hours. After centrifugation with 0.45 urn polytetrafluoroethylene (PTFE) filters, the filtrates were collected for HPLC analysis. The experimental results are shown in Table 7.

TABLE 7

| Category | Time | Hydrochloride Form CS3 | Hydrochloride Form A in CN105849100A |
|---|---|---|---|
| Solubility (μg/mL) | 1 hour | 2.5 | 0.3 |
| | 4 hours | 46.0 | 0.9 |
| | 24 hours | 15.0 | 2.5 |

It can be seen from the above results that the solubility of hydrochloride Form CS3 of the present disclosure is 6-51 times higher than that of hydrochloride Form A in CN1058491004 after 1, 4 and 24 hours in water.

Example 12 Stability of Hydrochloride Form CS3

Three samples of hydrochloride Form CS3 prepared by the present disclosure were stored in open dishes under conditions of 25° C./60% RH, 40° C./75% RH for 1 month, and 60° C./75% relative humidity for 2 weeks. The crystalline forms and the chemical purities were checked by XRPD and HPLC before and after storing. The results are shown in Table 8.

TABLE 8

| Initial crystalline form | Condition | Time | Change of crystalline form |
|---|---|---|---|
| Hydrochloride Form CS3 | 25° C./60% RH | Seven months | Unchanged |
| Hydrochloride Form CS3 | 40° C./75% RH | One month | Unchanged |
| Hydrochloride Form CS3 | 60° C./75% RH | Two weeks | Unchanged |

The results show that hydrochloride Form CS3 of the present disclosure is stable for at least 7 months at 25° C./60% RH, at least 1 month at 40° C./75% RH, and at least 2 weeks at 60° C./75% RH. No form changes and chemical purities decrease were observed and the purities were all above 98%. It can be seen that hydrochloride Form CS3 has good stability.

Example 13 Preparation of Hydrochloride Form CS4

Figure 10:
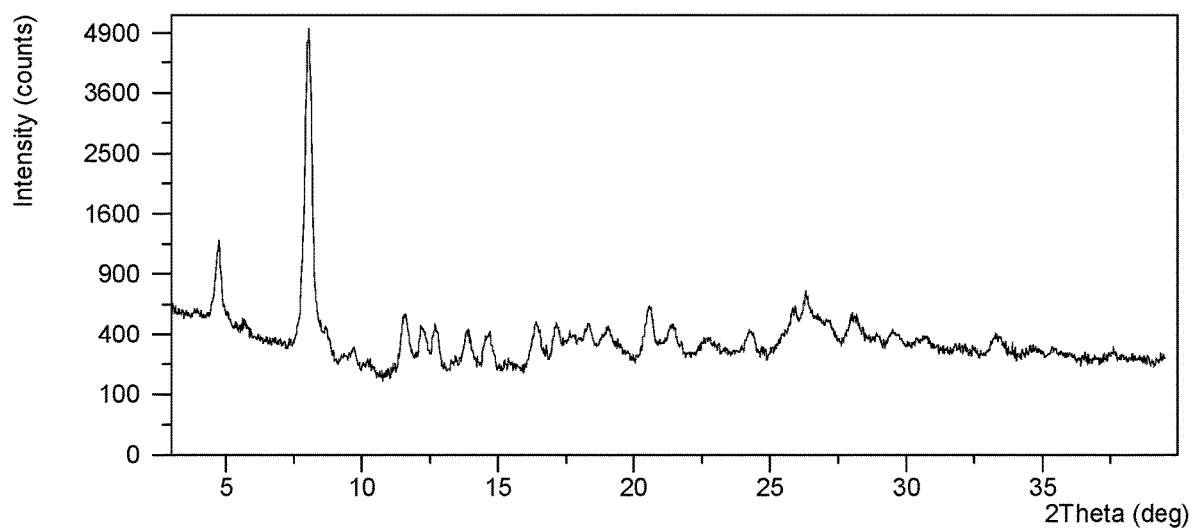
FIG. 10 shows an XRPD pattern of hydrochloride Form CS4 according to example 13 of the present disclosure.

9.7 mg of VX-787 hydrochloride Form C53 was weighed in a 1.5-mL glass vial. 0.4 mL of solvent mixture comprising isopropanol and water with a volume ratio 4:1 was added. The sample was stirred at room temperature (about 25° C.) for 30 minutes. 10.5 mg of VX-787 hydrochloride Form A (CN105849100A) was added. The sample was stirred at room temperature (about 25° C.) for 1 week, centrifuged, and dried under vacuum at room temperature. The solid obtained in this example was confirmed to be Form CS4, and the XRPD data is substantially as depicted in FIG. 10 and Table 9,

TABLE 9

| 2θ | d spacing | Intensity % |
|---|---|---|
| 4.73 | 18.69 | 22.98 |
| 5.67 | 15.60 | 6.74 |
| 8.04 | 10.99 | 100.00 |
| 8.73 | 10.13 | 5.00 |
| 9.71 | 9.11 | 2.70 |
| 10.21 | 8.66 | 1.05 |
| 11.57 | 7.65 | 7.25 |

TABLE 9-continued

| 2θ | d spacing | Intensity % |
|---|---|---|
| 12.19 | 7.26 | 5.52 |
| 12.70 | 6.97 | 5.64 |
| 13.87 | 6.39 | 4.69 |
| 14.65 | 6.05 | 4.46 |
| 16.39 | 5.41 | 6.27 |
| 17.14 | 5.17 | 5.69 |
| 18.33 | 4.84 | 5.73 |
| 19.05 | 4.66 | 5.03 |
| 20.57 | 4.32 | 8.49 |
| 21.40 | 4.15 | 5.32 |
| 22.68 | 3.92 | 3.21 |
| 24.27 | 3.67 | 4.28 |
| 25.87 | 3.44 | 7.31 |
| 26.32 | 3.39 | 10.66 |
| 27.15 | 3.28 | 5.80 |
| 28.00 | 3.19 | 6.62 |
| 29.55 | 3.02 | 3.87 |
| 30.70 | 2.91 | 3.13 |
| 33.29 | 2.69 | 3.30 |
| 34.69 | 2.59 | 1.40 |
| 35.42 | 2.53 | 1.38 |

Figure 16:
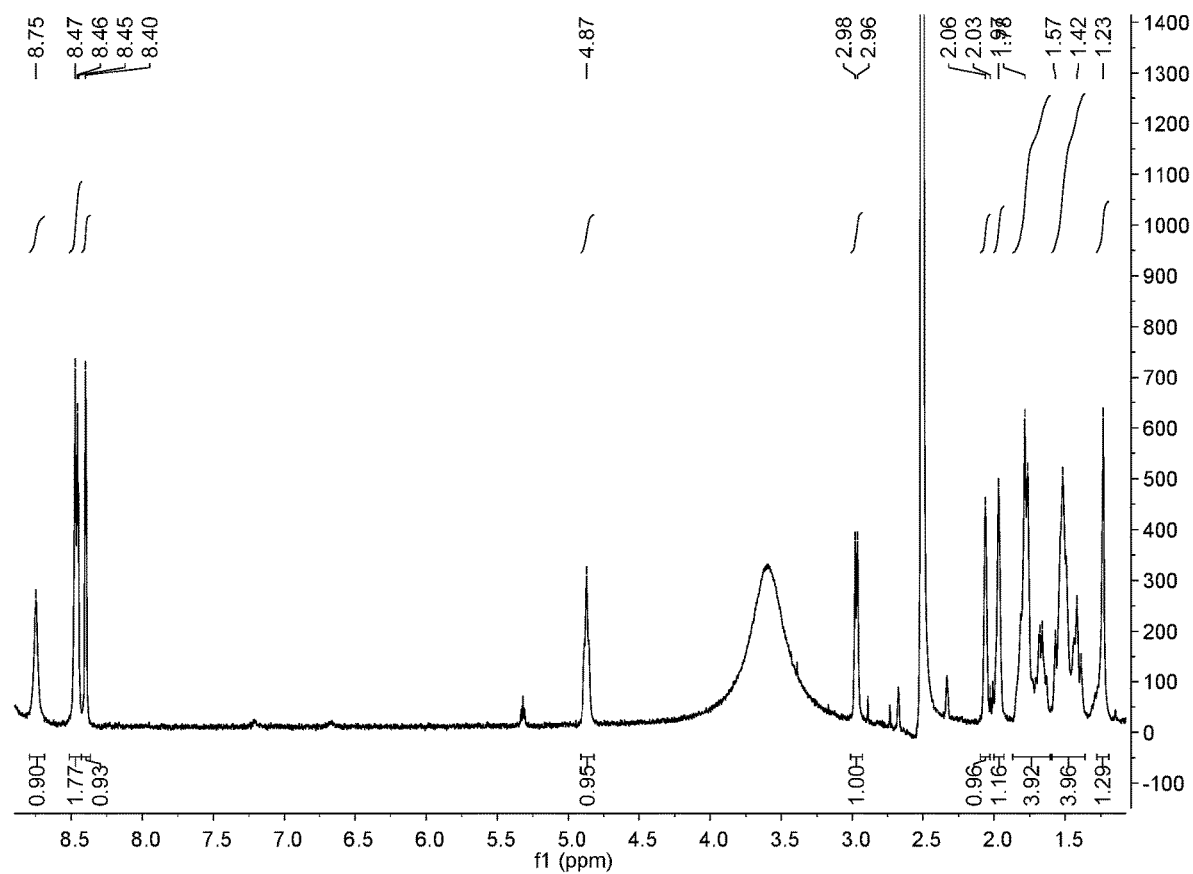
FIG. 16 shows a $^1$H NMR spectrum of hydrochloride Form CS4

No solvent signal was found in the liquid $^1$H NMR spectrum of hydrochloride Form CS4, The $^1$H NMR spectrum of hydrochloride Form CS4 is substantially as depicted in FIG. 16 and the corresponding data are: {$^1$H NMR (400 MHz, DMSO) δ 8.75 (s, 1H), 8.51-8.43 (m, 2H), 8.40 (m, 1H), 4.87 (m, 1H), 2.97 (d, J=6.4 Hz, 1H), 2.06 (m, 1H) 1.97 (m, 1H), 1.72 (dd, J=41.7, 7.4 Hz, 4H), 1.47 (dd, J=55.6, 16.2 Hz, 4H), 1.23 (s, 1H)}. The result shows that other than water, no solvent exists in hydrochloride Form CS4.

Figure 11:
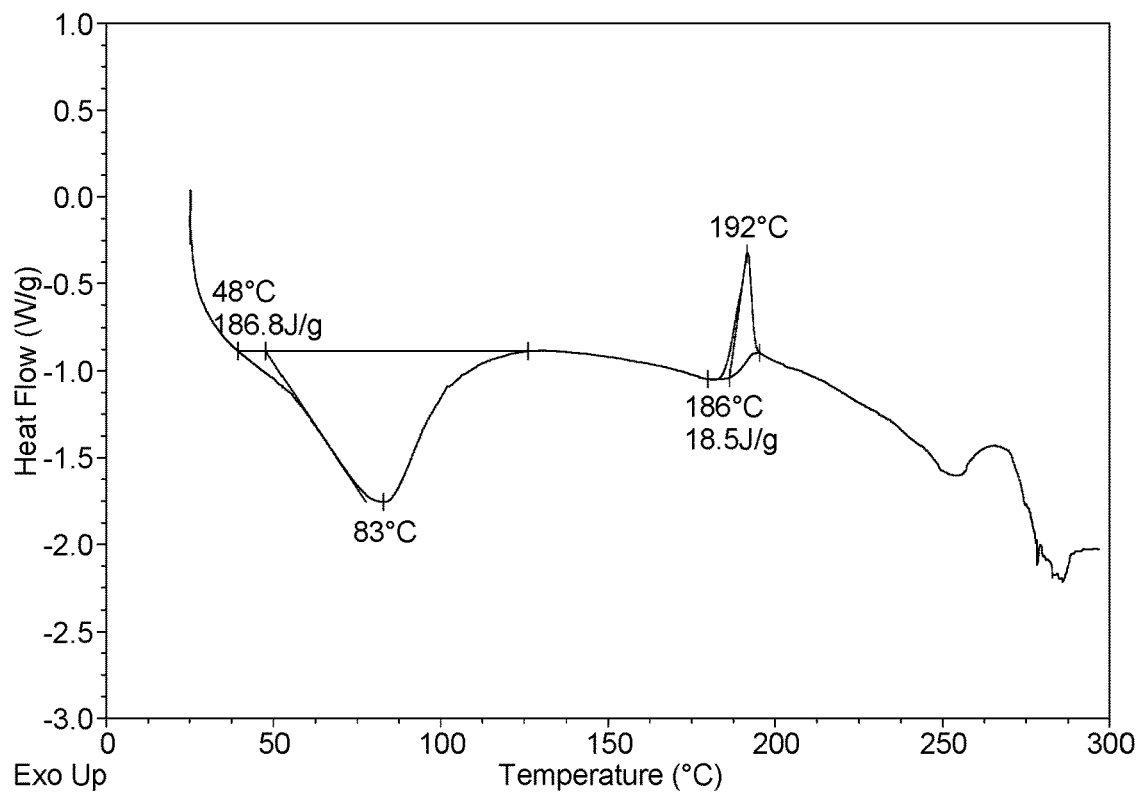
FIG. 11 shows a DSC curve of hydrochloride Form CS4 according to example 13 of the present disclosure.

The DSC curve of hydrochloride Form CS4 is substantially as depicted in FIG. 11, which shows an endothermic peak and an exothermic peak. The endothermic peak starts to appear at around 48° C. The endothermic peak is caused by water loss near the temperature, and the exothermic peak starts to appear at around 186° C.

Figure 12:
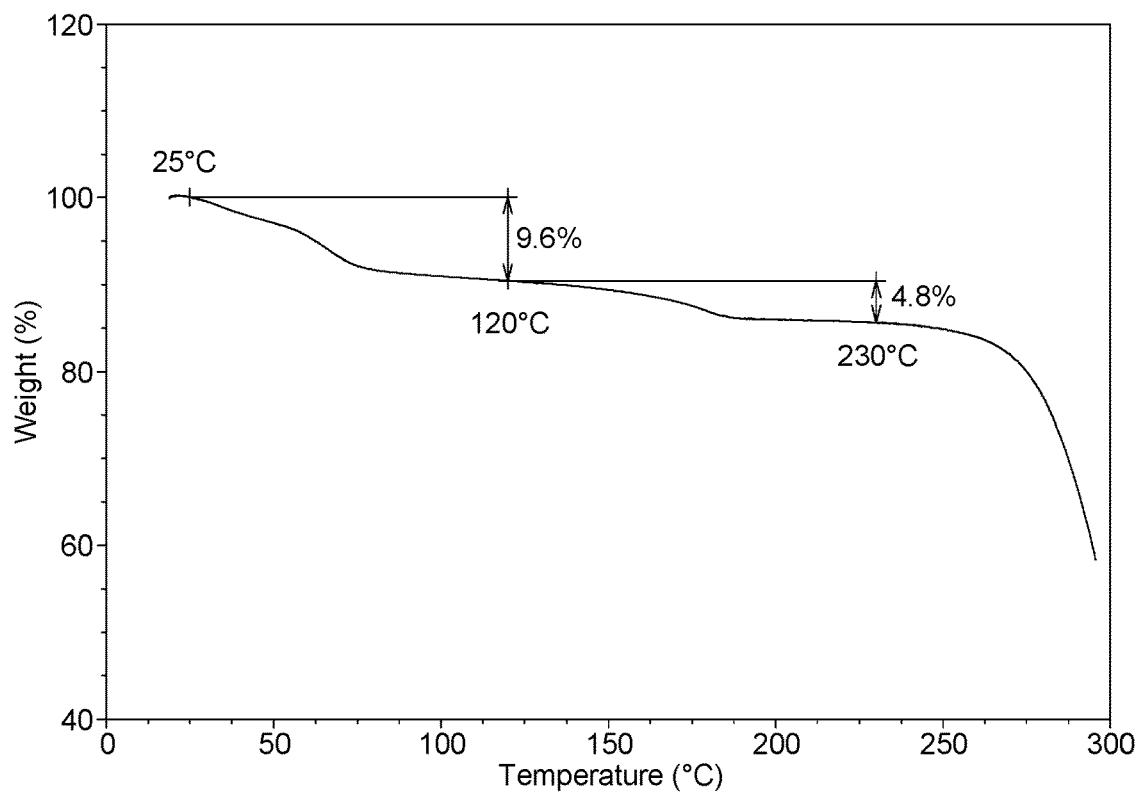
FIG. 12 shows a TGA curve of hydrochloride Form CS4 according to example 13 of the present disclosure

The TGA curve of hydrochloride Form CS4 is substantially as depicted in FIG. 12, which shows about 9.6% weight loss when heating to 120° C., and about 4.8% weight loss when heated to 230° C.

Example 14 Preparation of Hydrochloride Form CS4

Figure 18:
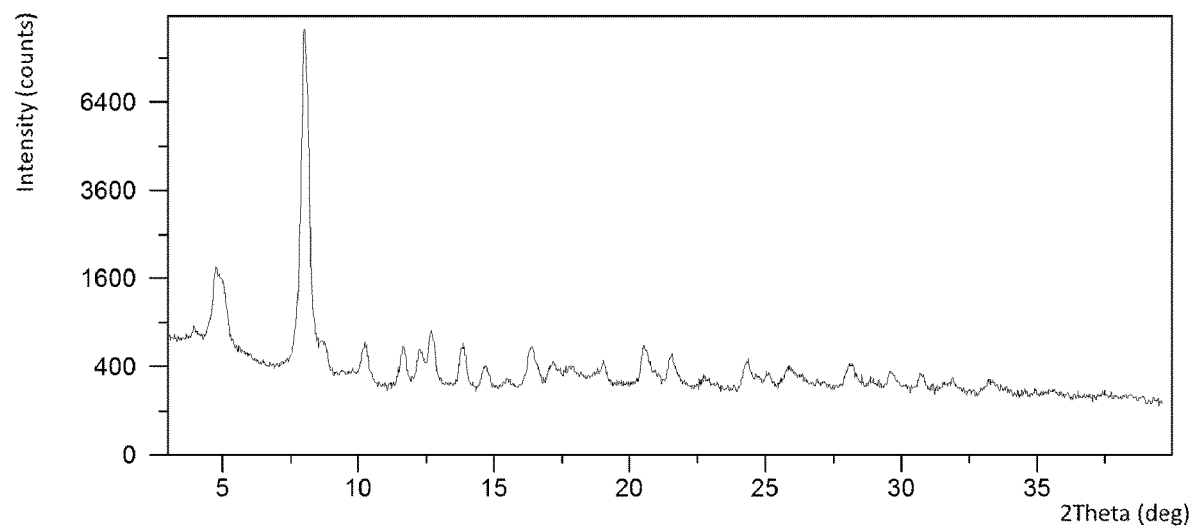
FIG. 18 shows an XRPD pattern of hydrochloride Form CS4 according to example 14 of the present disclosure.

200 mg of VX-787 hydrochloride was weighed into a 20 mL glass vial. 8 mL of solvent mixture of isopropanol and water (3:1, v/v) was added. The sample was stirred at room temperature (about 25° C.) for 5 days, then centrifuged to obtain a solid. The solid obtained in this example was confirmed to be hydrochloride Form CS4. The XRPD pattern is substantially as depicted in FIG. 18 and the XRPD data are shown in Table 10.

TABLE 10

| 2θ | d spacing | Intensity % |
|---|---|---|
| 4.76 | 18.56 | 13.64 |
| 8.03 | 11.01 | 100.00 |
| 8.17 | 10.82 | 62.73 |
| 8.69 | 10.18 | 3.62 |
| 10.26 | 8.62 | 3.85 |
| 11.66 | 7.59 | 3.98 |
| 12.29 | 7.20 | 3.47 |
| 12.69 | 6.98 | 6.02 |
| 12.80 | 6.92 | 4.64 |
| 13.85 | 6.40 | 4.42 |
| 14.68 | 6.03 | 1.78 |

TABLE 10-continued

| 2θ | d spacing | Intensity % |
|---|---|---|
| 15.48 | 5.72 | 0.54 |
| 16.38 | 5.41 | 4.14 |
| 17.17 | 5.16 | 2.26 |
| 17.84 | 4.97 | 1.77 |
| 19.04 | 4.66 | 2.38 |
| 20.55 | 4.32 | 4.20 |
| 21.53 | 4.13 | 3.13 |
| 22.78 | 3.90 | 0.94 |
| 24.33 | 3.66 | 2.63 |
| 25.08 | 3.55 | 1.27 |
| 25.89 | 3.44 | 1.92 |
| 27.01 | 3.30 | 0.65 |
| 28.13 | 3.17 | 2.31 |
| 29.64 | 3.01 | 1.68 |
| 30.75 | 2.91 | 1.54 |
| 31.84 | 2.81 | 1.01 |
| 33.30 | 2.69 | 1.01 |
| 35.54 | 2.53 | 0.32 |

Example 15 Stability of Hydrochloride Form CS4

Three samples of hydrochloride Form CS4 prepared by the present disclosure were stored in open dishes under conditions of 25° C./60% RH for two weeks, 40° C./75% RH for 1 month, and 60° C./75% relative humidity for 2 weeks. The crystalline forms and the chemical purities were checked by XRPD and HPLC respectively before and after storing. The results are shown in Table 11.

TABLE 11

| Initial crystalline form | Condition | Time | Change of crystalline form |
|---|---|---|---|
| Hydrochloride Form CS4 | 25° C./60% RH | Two weeks | Unchanged |
| Hydrochloride Form CS4 | 40° C./75% RH | One month | Unchanged |
| Hydrochloride Form CS4 | 60° C./75% RH | Two weeks | Unchanged |

The results show that hydrochloride Form CS4 is stable for at least 2 weeks at 25° C./60% RH, at least 1 month at 40° C./75% RH, and at least 2 weeks at 60° C./75% RH. No form changes were observed of the crystalline form and no obvious chemical purity change was observed. The purities were all above 98%. It can be seen that hydrochloride Form CS4 provided by the disclosure has good stability.

Example 16 Purification Effect of Hydrochloride Form CS4

Chemical purities of Hydrochloride Form A in CN105849100A and hydrochloride Form CS4 of the present disclosure prepared from the same raw materials were checked by HPLC.

The HPLC purity test results show that hydrochloride Form CS4 of the present disclosure has a remarkable purification effect. The purity of hydrochloride Form A of CN105849100A is 97.91%, and the purity of hydrochloride Form CS4 of the present disclosure is 99.70%, The purity of Form CS4 of the present disclosure is higher than the purity of hydrochloride Form A in CN105849100A.

Example 17 Dynamic Solubility Comparison of Hydrochloride Form CS4 and Hydrochloride Form A in CN105849100A Hydrochloride Form CS4 of the present disclosure and hydrochloride Form A in CN105849100A were prepared into saturated solution in pure water. The content of the sample in the saturated solution was determined by high performance liquid chromatography (HPLC) after 1, 4 and 24 hours. The solubility data of hydrochloride Form CS4 of the present disclosure and hydrochloride Form A in CN105849100A are shown in Table 12.

TABLE 12

| Category | Time | Hydrochloride Form CS4 | Hydrochloride Form A in CN105849100A |
|---|---|---|---|
| Solubility (μg/mL) | 1 hour | 85 | 0.3 |
|  | 4 hours | 75 | 0.9 |
|  | 24 hours | 94 | 2.5 |

It can be seen from the above comparison results that the solubility of hydrochloride Form CS4 of the present disclosure is 38-283 times higher than that of the hydrochloride Form A of CN105849100A after equlibrated for 1, 4 and 24 hours in water.

Example 18 Preparation of Crystalline Form CS9 of Compound I 308.3 mg of VX-787 was weighed into a 20-mL glass vial, 10 mL of solvent mixture comprising methanol and toluene with a volume ratio of 1:3 was added. The sample was stirred at room temperature (about 25° C.) for 72 hours, and then centrifuged and dried under vacuum at room temperature to obtain the solid.

Figure 19:
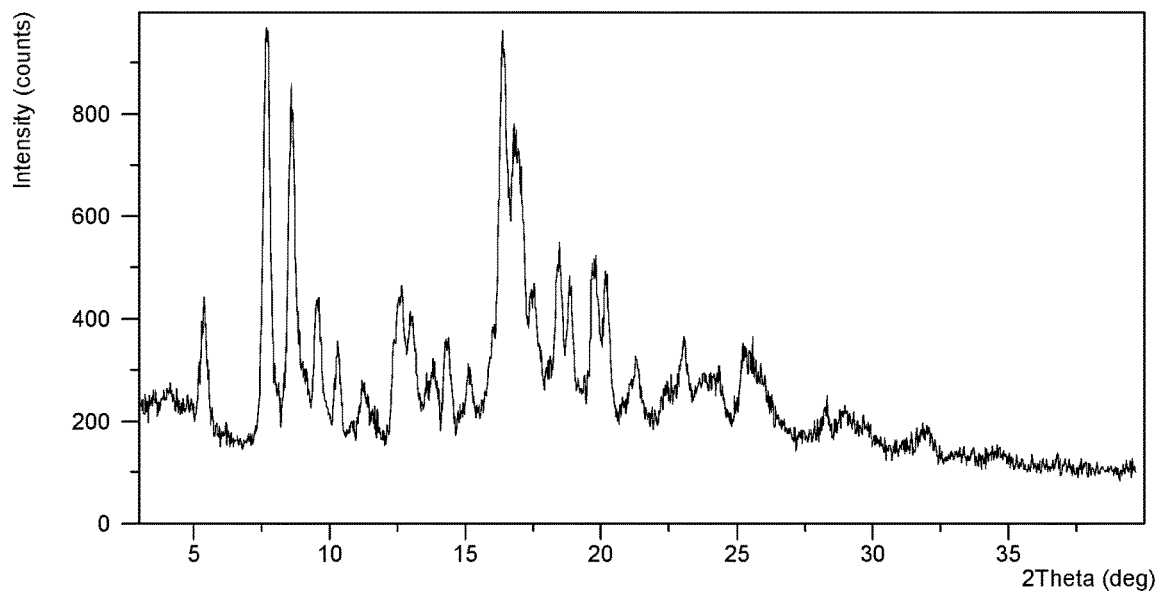
FIG. 19 shows an XRPD pattern of crystalline form CS9 of compound I according to example 18 of the present disclosure.
Figure 20:
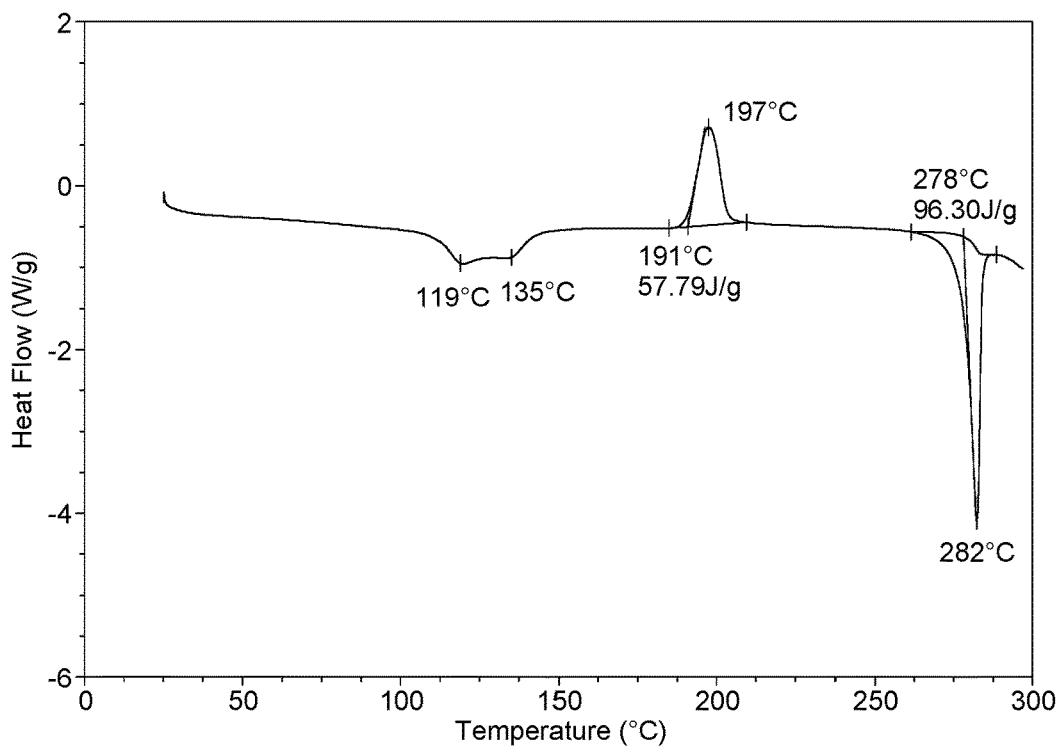
FIG. 20 shows a DSC curve of crystalline form CS9 of compound I according to example 18 of the present disclosure.
Figure 21:
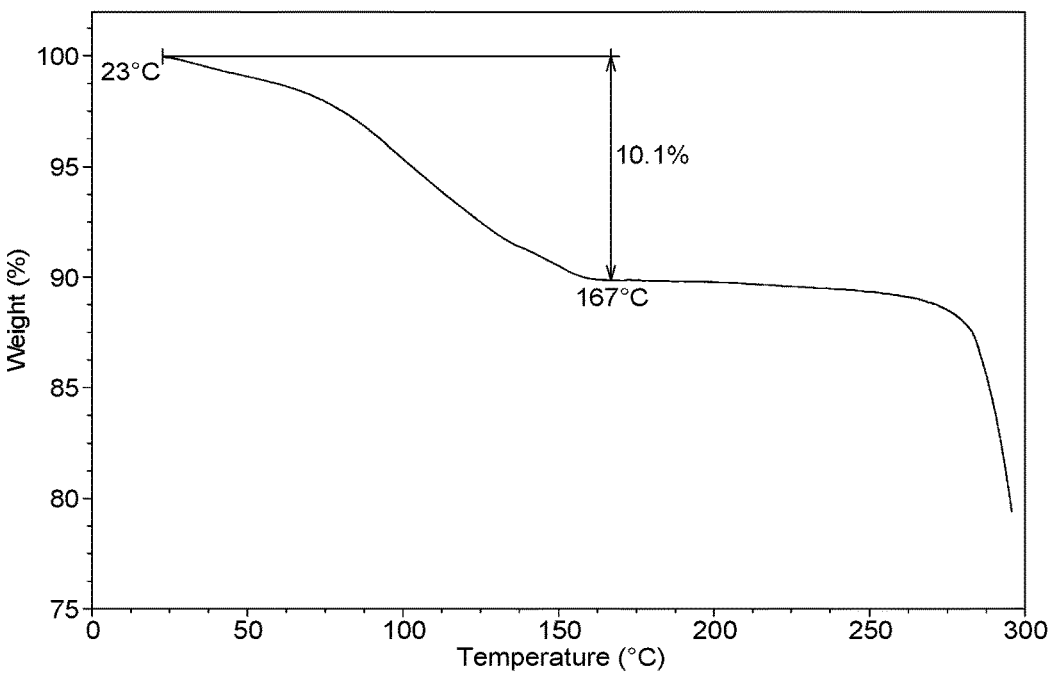
FIG. 21 shows a TGA curve of crystalline form CS9 of compound I according to example 18 of the present disclosure.

The X-ray powder diffraction data of the crystalline form obtained in this example is shown in Table 13. The XRPD pattern is shown in FIG. 19, the DSC curve is shown in FIG. 20, and the TGA curve is shown in FIG. 21.

TABLE 13

| 2θ | d spacing | Intensity % |
|---|---|---|
| 5.37 | 16.44 | 28.12 |
| 7.68 | 11.50 | 100.00 |
| 8.59 | 10.29 | 86.39 |
| 9.56 | 9.25 | 33.86 |
| 10.32 | 8.57 | 22.49 |
| 11.25 | 7.86 | 12.22 |
| 12.62 | 7.02 | 33.81 |
| 13.01 | 6.80 | 28.67 |
| 13.81 | 6.41 | 15.99 |
| 14.32 | 6.19 | 22.48 |
| 15.13 | 5.85 | 15.47 |
| 16.39 | 5.41 | 96.82 |
| 17.09 | 5.19 | 56.02 |
| 18.43 | 4.81 | 43.41 |
| 18.84 | 4.71 | 35.25 |
| 19.74 | 4.50 | 39.15 |
| 20.19 | 4.40 | 36.34 |
| 21.28 | 4.17 | 16.60 |
| 23.04 | 3.86 | 20.36 |
| 24.04 | 3.70 | 11.10 |
| 25.32 | 3.52 | 17.74 |
| 31.93 | 2.80 | 5.66 |

Example 19 Preparation of Crystalline Form CS3 of Compound I 29.0 mg of crystalline form CS9 was weighed into a 1.5-mL glass vial, followed by adding 1 ml, of solvent mixture comprising tetrahydrofuran and dichloromethane with a volume ratio of 1:4. The sample was stirred at 50° C. for 72 hours, and then centrifuged and dried under vacuum at room temperature to obtain the solid.

Figure 22:
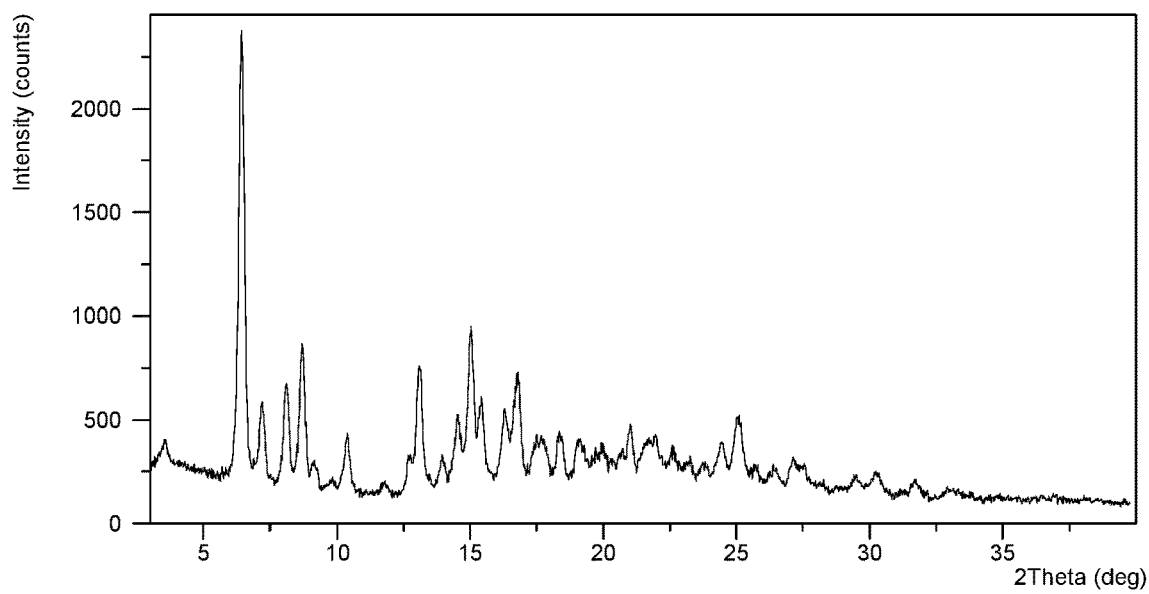
FIG. 22 shows an XRPD pattern of crystalline form CS3 of compound I according to example 19 of the present disclosure.
Figure 23:
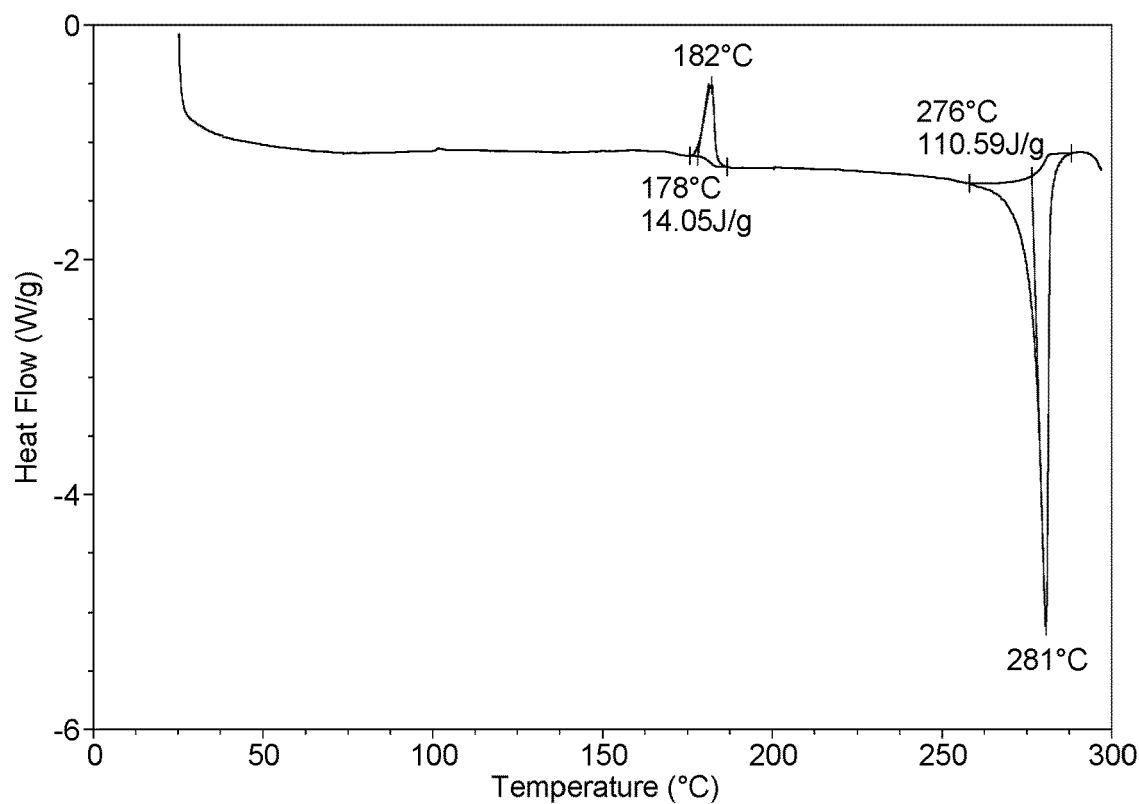
FIG. 23 shows a DSC curve of crystalline form CS3 of compound I according to example 19 of the present disclosure.
Figure 24:
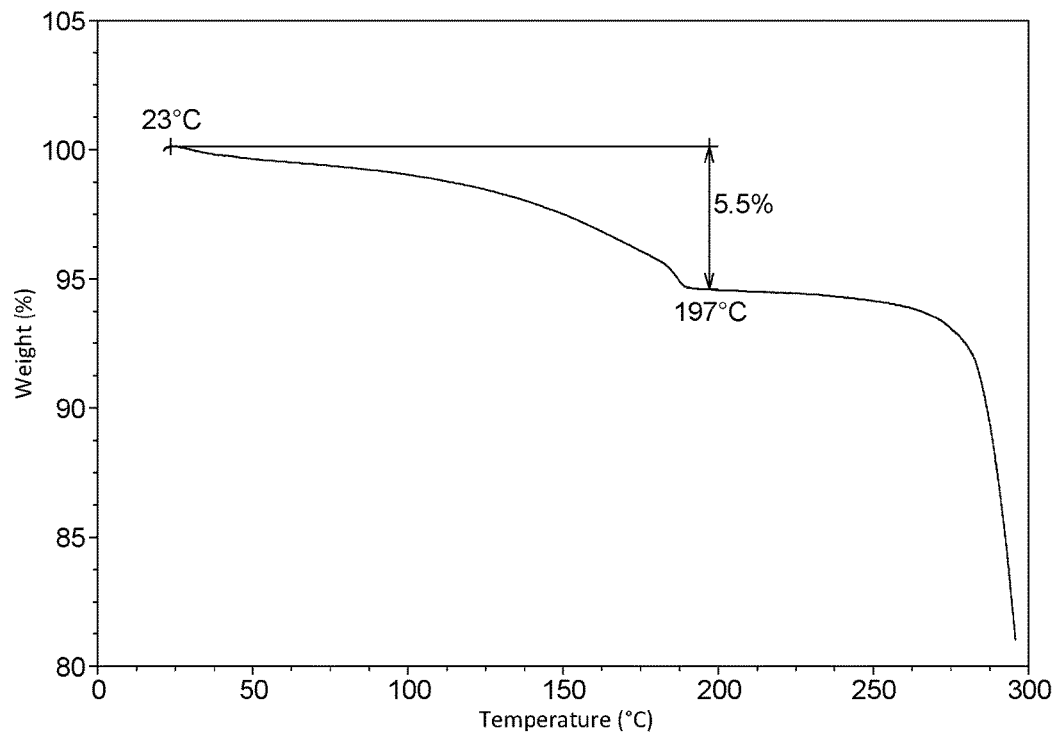
FIG. 24 shows a TGA curve of crystalline form CS3 of compound I according to example 19 of the present disclosure.

The X-ray powder diffraction data of the crystalline form obtained in this example is shown in Table 14, the sample obtained was confirmed to be Form CS3. The XRPD pattern is shown in FIG. 22, the DSC curve is shown in FIG. 23, and the TGA curve is shown in FIG. 24.

TABLE 14

| 2θ | d spacing | Intensity % |
| --- | --- | --- |
| 3.52 | 25.08 | 12.23 |
| 6.44 | 13.73 | 100.00 |
| 7.20 | 12.28 | 20.93 |
| 8.09 | 10.93 | 24.66 |
| 8.70 | 10.17 | 33.42 |
| 9.13 | 9.68 | 7.77 |
| 10.38 | 8.52 | 14.10 |
| 11.79 | 7.50 | 3.33 |
| 12.73 | 6.95 | 9.09 |
| 13.11 | 6.75 | 28.18 |
| 13.97 | 6.34 | 8.79 |
| 14.55 | 6.09 | 18.06 |
| 15.03 | 5.89 | 36.08 |
| 15.43 | 5.74 | 20.73 |
| 16.31 | 5.44 | 19.27 |
| 16.80 | 5.28 | 27.50 |
| 17.63 | 5.03 | 12.27 |
| 18.36 | 4.83 | 14.03 |
| 19.08 | 4.65 | 12.05 |
| 19.93 | 4.46 | 10.73 |
| 21.00 | 4.23 | 15.63 |
| 21.86 | 4.07 | 12.40 |
| 22.61 | 3.93 | 10.64 |
| 23.77 | 3.74 | 7.36 |
| 24.45 | 3.64 | 12.23 |
| 25.07 | 3.55 | 17.31 |
| 26.41 | 3.38 | 6.55 |
| 27.15 | 3.28 | 8.58 |
| 29.47 | 3.03 | 4.75 |
| 30.25 | 2.95 | 5.35 |
| 31.70 | 2.82 | 3.96 |
| 33.08 | 2.71 | 1.97 |

Example 20 Stability of Crystalline Form CS3 of Compound

Two solid samples of crystalline form CS3 of compound I of the present disclosure (initial purity: 99.24%) were stored under conditions of 25° C./60% RH and 40° C./75% RH for 5 months in open dishes. The crystalline forms and chemical purities were checked by HPLC and XRPD before and after storing. The experimental results are shown in Table 15.

TABLE 15

| Initial Crystalline Form | Condition | Change of Time Crystalline Form | Purity |
| --- | --- | --- | --- |
| CS3 | 25° C./60% RH | Five months Unchanged | 99.28% |
| CS3 | 40° C./75% RH | Five months Unchanged | 99.26% |

The results show that crystalline form CS3 of compound I of the present disclosure is stable for at least 5 months at 25° C./60% RH and 40° C./75% RH. No crystalline form change and chemical purity decrease were observed. It can be seen that crystalline form CS3 of compound I of the present disclosure has good stability.

Example 22 Dynamic Solubility Comparison of Crystalline Form CS3 of Compound I and Free Form Form A in CN1.05849100A The crystallite form CS3 of compound I of the present disclosure and free form Form A in CN105849100A are prepared into saturated solutions in pH-5.0 FeSSIF (Fed state simulated intestinal fluids) and pH=6.5 FaSSIF (Fasted state simulated intestinal fluids). The content of the sample in the saturated solution was determined by high performance liquid chromatography (HPLC) after equlibrated for 1, 4 and 24 hours. The solubility results are shown in Table 16.

TABLE 16

| | Solubility | | | | | |
| --- | --- | --- | --- | --- | --- | --- |
| | FaSSIF (µg/mL) | | | FeSSIF (µg/mL) | | |
| Name | 1 hour | 4 hours | 24 hours | 1 hour | 4 hours | 24 hours |
| Form CS3 of Compound I | 110 | 210 | 200 | 210 | 290 | 250 |
| Free Form Form A in CN105849100A | 7 | 13 | 31 | 18 | 30 | 57 |

The results show that after equlibrated for 1, 4 and 24 hours in FaSSIF and FeSSIF, the solubility of crystalline form CS3 of compound I of the present disclosure is higher than that of free form crystalline Form A. In FeSSIF, solubility of crystalline Form CS3 is about 4-11 times higher than that of Form A in CN105849100A and in FaSSIF, solubility of crystalline Form CS3 is about 6-16 times higher than that of Form A in CN105849100.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form of compound I hydrochloride,

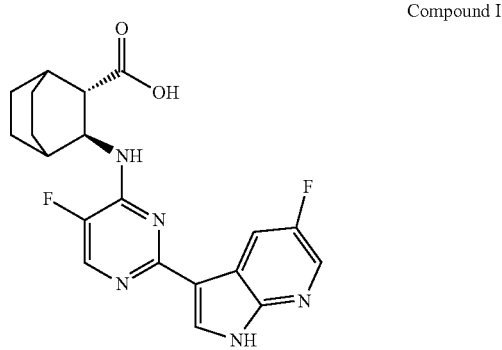 [SMILES: O=C(O)[C@H]1C2CCC(CC2)[C@@H]1Nc1nc(-c2c[nH]c3ncc(F)cc23)ncc1F]

Compound I wherein
the crystalline form of compound I hydrochloride is compound I hydrochloride hydrate Form CS3 or compound I hydrochloride acetic acid solvate Form CS1, and
the X-ray powder diffraction pattern shows characteristic peaks at 2 theta values of 7.1°±0.2°, 27.0°±0.2° and 15.7°±0.2° using CuKα radiation.

2. A process for preparing the compound I hydrochloride hydrate Form CS3 according to claim 1, wherein the process comprises:

placing crystalline form CS1 of compound I hydrochloride into inert atmosphere,
heating to 100-200° C.,
holding for 5-20 minutes, and
transferring to room temperature to obtain a solid of compound I hydrochloride Form CS3.

3. A crystalline form CS4 of compound I hydrochloride,

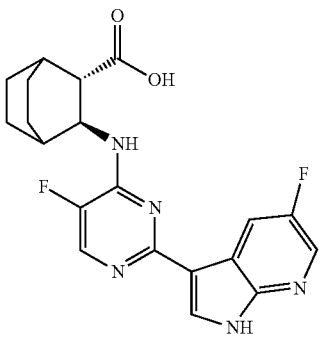

Compound I wherein the X-ray powder diffraction pattern shows characteristic peaks at 2 theta values of 8.0°±0.2°, 4.7°±0.2°, 20.6°±0.2° and 11.6°±0.2° using CuKα radiation.

4. The crystalline form CS4 of compound I hydrochloride according to claim 3, wherein the X-ray powder diffraction pattern shows one or two or three characteristic peaks at 2 theta values of 16.4°±0.2°, 17.1°±0.2° and 12.7°±0.2° using CuKα radiation.

5. A process for preparing the crystalline form CS4 of compound I hydrochloride according to claim 3, wherein the process comprises:
adding compound I hydrochloride to a solvent mixture comprising an alcohol and water, wherein a volume ratio of the alcohol to water is 19/1-1/19,
stirring at 5-30° C. for 1-7 days, and
filtering and drying to obtain the crystalline form CS4 of compound I hydrochloride.

6. A crystalline form CS3 of compound I,

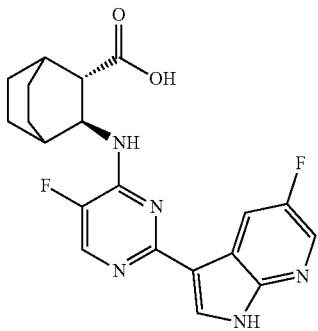

Compound I wherein the X-ray powder diffraction pattern shows characteristic peaks at 2 theta values of 6.4°±0.2°, 15.0°±0.2° and 8.7°±0.2° using CuKα radiation.

7. The crystalline form CS3 of compound I according to claim 6, wherein the X-ray powder diffraction pattern shows one or two characteristic peaks at 2 theta values of 13.1°±0.2° and 8.1°±0.2° using CuKα radiation.

8. The crystalline form CS3 of compound I according to claim 6, wherein the X-ray powder diffraction pattern shows one or two or three characteristic peaks at 2 theta values of 7.2°±0.2°, 16.3°±0.2° and 10.4°±0.2° using CuKα radiation.

9. A process for preparing the crystalline form CS3 according to claim 6, wherein the process comprises:
adding the solid of compound I into a solvent mixture comprising an ether and a halohydrocarbon, stirring at 50° C., and
isolating and drying the solid to obtain crystalline form CS3.

10. The process for preparing the crystalline form CS3 according to claim 9, wherein said ether is tetrahydrofuran, and said halohydrocarbon is dichloromethane.

11. A pharmaceutical composition, wherein said pharmaceutical composition comprises a therapeutically effective amount of the crystalline form CS3 according to claim 6 and pharmaceutically acceptable carriers, diluents or excipients.

12. A method for inhibiting virus protein, comprising administering to a patient in need thereof a therapeutically effective amount of the crystalline form CS3 of compound I according to claim 6.

13. A method for treating influenza A, comprising administering to a patient in need thereof a therapeutically effective amount of the crystalline form CS3 of compound I according to claim 6.

14. A pharmaceutical composition, wherein said pharmaceutical composition comprises a therapeutically effective amount of the crystalline form CS4 of compound I hydrochloride according to claim 3 and pharmaceutically acceptable carriers, diluents or excipients.

15. A method for inhibiting virus protein, comprising administering to a patient in need thereof a therapeutically effective amount of the crystalline form CS4 of compound I hydrochloride according to claim 3.

16. The crystalline form of compound I hydrochloride according to claim 1, wherein the X-ray powder diffraction pattern shows one or two or three characteristic peaks at 2 theta values of 25.8°±0.2°, 14.7°±0.2° and 23.9°±0.2° using CuKα radiation.

17. The crystalline form of compound I hydrochloride according to claim 1, wherein the X-ray powder diffraction pattern shows one or two or three characteristic peaks at 2 theta values of 17.5°±0.2°, 13.5°±0.2° and 28.7°±0.2° using CuKα radiation.

18. A pharmaceutical composition, wherein said pharmaceutical composition comprises a therapeutically effective amount of the crystalline form of compound I hydrochloride according to claim 1 and pharmaceutically acceptable carriers, diluents or excipients.

19. A method for inhibiting virus protein, comprising administering to a patient in need thereof a therapeutically effective amount of the crystalline form of compound I hydrochloride according to claim 1.

* * * * *